(12) United States Patent
Osadchy et al.

(10) Patent No.: US 6,368,285 B1
(45) Date of Patent: Apr. 9, 2002

(54) METHOD AND APPARATUS FOR MAPPING A CHAMBER OF A HEART

(75) Inventors: Margarita Osadchy; Daniel Reisfeld, both of Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/643,667

(22) Filed: Aug. 18, 2000

Related U.S. Application Data

(63) Continuation-in-part of application No. 09/399,477, filed on Sep. 21, 1999.

(51) Int. Cl.[7] ................................................ A61B 5/02
(52) U.S. Cl. ...................... 600/508; 606/130; 382/131; 382/173; 382/174
(58) Field of Search ................................ 600/441, 409, 600/407, 508, 310, 342, 377, 374, 424, 425, 450, 463, 467, 468, 481, 483; 606/45, 130; 382/131, 173, 174

(56) References Cited

U.S. PATENT DOCUMENTS

| 3,316,896 A | 5/1967 | Thomasset |
| 4,157,572 A | 6/1979 | Kennedy et al. ............... 360/33 |
| 4,173,228 A | * 11/1979 | Steenwyk et al. .......... 600/409 |
| 4,459,990 A | 7/1984 | Barnea ....................... 128/656 |

(List continued on next page.)

FOREIGN PATENT DOCUMENTS

| EP | 0 501 993 B1 | 6/1997 |
| EP | 0 974 936 A2 | 1/2000 |
| WO | WO 94/04938 | 3/1994 |

(List continued on next page.)

OTHER PUBLICATIONS

Freeman, H.; "Computer Processing of Line Drawing Images"; Computing Surveys 6, 1974, pp. 57–97.

Gerstenfeld E., Sahakian A., Swiryn S.; Evidence for Transient Linking of Atrial Excitation During Artial Fibrillation in Humans (1992); Circulation vol. 86, No. 2, pp. 375–382.

Gerstenfeld E., Sahakian A., Baerman J., Ropella K., Swiryn S.; Detection of Changes in Atrial Endocardial Activation With Use of an Orthogonal Catheter (1991); JACC vol. 18, No. 4, pp. 1034–1042.

(List continued on next page.)

*Primary Examiner*—Marvin M. Lateef
*Assistant Examiner*—Jeoyuh Lin
(74) *Attorney, Agent, or Firm*—Louis J. Capezzuto

(57) ABSTRACT

A method for intracardially mapping a condition such as an electrical or mechanical property of a chamber of a heart uses a catheter having a distal tip and at least one condition sensor contained therein or proximate thereto. The at least one sensor is capable of sensing condition information in the chamber and provides the three-dimensional position of the catheter tip in a positional frame of reference. The method includes the steps of acquiring first and second images of the chamber. The images are acquired from different projections and contain topological information of the chamber. The chamber images are registered with the positional frame of reference. The catheter distal tip is advanced into the catheter and is navigated to acquisition points under the guidance of topological information contained in or derived from the images. Condition and position information are acquired at each of the acquisition points, the points being sufficient in number and spacing to permit the generation of a map of the condition in the chamber. The topological information used to guide the navigation of the catheter is preferably a three-dimensional reconstruction of the chamber derived from the topological information contained in the images.

88 Claims, 17 Drawing Sheets

U.S. PATENT DOCUMENTS

| | | | |
|---|---|---|---|
| 4,522,212 A | 6/1985 | Gelinas et al. | 128/642 |
| 4,628,937 A | 12/1986 | Hess et al. | 128/642 |
| 4,630,203 A | 12/1986 | Szirtes | 364/414 |
| 4,660,571 A | 4/1987 | Hess et al. | 128/784 |
| 4,682,603 A | 7/1987 | Franz | 128/642 |
| 4,699,147 A | 10/1987 | Chilson et al. | 128/642 |
| 4,762,124 A | 8/1988 | Kerch et al. | 128/156 |
| 4,875,165 A | 10/1989 | Fencil et al. | 364/413.22 |
| 4,878,115 A | 10/1989 | Elion | 358/111 |
| 4,898,181 A | 2/1990 | Kessier | 128/699 |
| 4,905,705 A | 3/1990 | Kizakevich et al. | 128/696 |
| 4,911,174 A | 3/1990 | Pederson et al. | 128/695 |
| 4,922,912 A | 5/1990 | Watanabe | 128/642 |
| 4,940,064 A | 7/1990 | Desai | 128/784 |
| 4,955,382 A | 9/1990 | Franz et al. | 128/642 |
| 4,962,767 A | 10/1990 | Brownlee | 128/786 |
| 4,979,510 A | 12/1990 | Franz et al. | 128/642 |
| 5,022,396 A | 6/1991 | Watanabe | 128/642 |
| 5,038,791 A | 8/1991 | Collins et al. | 128/696 |
| 5,042,486 A | 8/1991 | Pfeiler et al. | 128/653 |
| 5,056,524 A | 10/1991 | Oe | 128/642 |
| 5,127,403 A | 7/1992 | Brownlee | 128/419 P |
| 5,156,151 A | 10/1992 | Imran | 128/642 |
| 5,175,773 A | 12/1992 | Garreau et al. | 382/6 |
| 5,215,103 A | 6/1993 | Desai | 128/784 |
| 5,227,969 A | 7/1993 | Waggener et al. | 364/413.26 |
| 5,228,442 A | 7/1993 | Imran | 128/642 |
| 5,231,995 A | 8/1993 | Desai | 128/784 |
| 5,239,999 A | 8/1993 | Imran | 128/642 |
| 5,243,981 A | 9/1993 | Hudrlik | 607/11 |
| 5,255,678 A | 10/1993 | Deslauriers et al. | 128/642 |
| 5,255,679 A | 10/1993 | Imran | 128/642 |
| 5,279,299 A | 1/1994 | Imran | 128/642 |
| 5,293,869 A | 3/1994 | Edwards et al. | 128/642 |
| 5,297,549 A | 3/1994 | Beatty et al. | 128/642 |
| 5,311,866 A | 5/1994 | Kagan et al. | 128/642 |
| 5,313,943 A | 5/1994 | Houser et al. | 128/642 |
| 5,324,284 A | 6/1994 | Imran | 606/15 |
| 5,341,807 A | 8/1994 | Nardella | 128/642 |
| 5,345,936 A | 9/1994 | Pomeranz et al. | 138/642 |
| 5,383,917 A | 1/1995 | Desai et al. | 607/702 |
| 5,391,199 A | 2/1995 | Ben-Haim | 607/122 |
| 5,409,000 A | 4/1995 | Imran | 128/642 |
| 5,433,198 A | 7/1995 | Desai | 128/642 |
| 5,443,489 A | 8/1995 | Ben-Haim | 607/115 |
| 5,454,370 A | 10/1995 | Avitall | 128/642 |
| 5,485,849 A | 1/1996 | Panescu et al. | 128/699 |
| 5,487,391 A | 1/1996 | Panescu | 128/699 |
| 5,531,227 A | 7/1996 | Schneider | 128/653.1 |
| 5,546,951 A | 8/1996 | Ben-Haim | 128/702 |
| 5,549,109 A | 8/1996 | Samson et al. | 128/642 |
| 5,588,432 A | 12/1996 | Crowley | 128/660.03 |
| 5,595,183 A | 1/1997 | Swanson et al. | 128/697 |
| 5,637,090 A | 6/1997 | McGee et al. | 604/95 |
| 5,657,755 A | 8/1997 | Desai | 128/642 |
| 5,694,945 A * | 12/1997 | Ben-Haim | 128/736 |
| 5,697,377 A | 12/1997 | Wittkampf | 128/696 |
| 5,718,241 A | 2/1998 | Ben-Haim et al. | 128/702 |
| 5,730,704 A | 3/1998 | Avitall | 600/374 |
| 5,738,096 A | 4/1998 | Ben-Haim | 128/653.1 |
| 5,755,664 A | 5/1998 | Rubenstein | 600/377 |
| 5,840,031 A | 11/1998 | Crowley | 600/440 |
| 5,842,984 A | 12/1998 | Avitall | 600/374 |
| 5,871,019 A * | 2/1999 | Belohlavek | 600/441 |
| 5,889,524 A | 3/1999 | Sheehan et al. | 345/419 |
| 5,921,924 A | 7/1999 | Avitall | 600/374 |
| 5,931,835 A | 8/1999 | Mackey | 606/34 |
| 5,931,863 A | 8/1999 | Griffin, III et al. | 607/122 |
| 5,964,757 A * | 10/1999 | Ponzi | 606/45 |
| 5,999,587 A | 12/1999 | Ning et al. | 378/4 |
| 6,052,618 A | 4/2000 | Dahlke et al. | 600/523 |
| 6,066,094 A | 5/2000 | Ben-Haim | 600/437 |

FOREIGN PATENT DOCUMENTS

| | | |
|---|---|---|
| WO | WO 96/05768 | 2/1996 |
| WO | WO 97/24983 | 6/1997 |
| WO | WO 98/12663 | 3/1998 |
| WO | WO 98/35720 A3 | 8/1998 |
| WO | WO 98/35720 A2 | 8/1998 |
| WO | WO 99/05971 | 2/1999 |

OTHER PUBLICATIONS

Kadish A., Spear J., Levine J., Hanich R., Prood C., Moore E.; Vector Mapping of Myocardial Activation (1986); Laboratory Investigation Arrhythmia vol. 74, No. 3, pp. 603–615.

Kass et al.; Proceedings of First International Conference Vision (1987); Snakes: Active Contour Models; pp. 259–268.

Terzopoulos D.; Transactions on Pattern Analysis and Machine Intelligence (1986), vol. PAMI–8, No. 4; Regularization of Inverse Visual Problems Involving Discontinuities; pp. 413–424.

Lai et al.; IEEE Transactions on Pattern Analysis and Machine Intelligence (1995) vol. 17, No. 11; Deformable Contours: Modeling and Extraction; pp. 1084–1090.

Onnasch et al.; Computers in Cardiology, Long Beach, CA, IEEE Computer Society (1975); A Versatile Program for the Documentation and Comparison of Traced Heart Contours; pp. 257–262.

Duda et al.; Communications of the ACM (1972) vol. 15, No. 1; Use of the Hough Transormation to Detect Lines and Curves in Pictures; pp. 11–15.

Castleman, K.R.; Digital Image Processing (1996); "Curve and Surface Fitting"; pp. 501–507.

Jain, A.K.; Fundamentals of Digital Image Processing (1989); "The Back–Projection Operator"; pp. 445.

Foley J.D., van Dam A., Feiner S.K., Hughes J.F.; 2nd Edition in C Computer Graphics Principles and Practice (1996); "Filling Algorithms"; pp. 979–986.

* cited by examiner

METHOD AND APPARATUS FOR MAPPING A CHAMBER OF A HEART

CROSS-REFERENCE TO RELATED APPLICATIONS

This application is a continuation-in-part of copending U.S. patent application Ser. No. 09/399,477 filed on Sep. 21, 1999, which is incorporated herein in its entirety by reference.

FIELD OF THE INVENTION

The invention relates generally to methods and apparatus for mapping a condition or property of an organ of a subject, and particularly to methods and apparatus for mapping the electrical and/or the mechanical activity of one or more chambers of the heart.

BACKGROUND OF THE INVENTION

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

U.S. Pat. No. 5,546,951 and U.S. patent application Ser. No. 08/793,371 and its corresponding application filed under the Patent Cooperation Treaty and published as WO 96/05768, which are incorporated herein in their entirety by reference, disclose methods for sensing an electrical property of the heart tissue, for example, local activation time, as a function of the precise location within the heart. The data are acquired with one or more catheters that are advanced into the heart, the catheters having electrical and location sensors in their distal tips. Methods of creating a map of the electrical activity of the heart based on these data are disclosed in commonly assigned U.S. patent application Ser. No. 09/122,137 filed on Jul. 24, 1998 and in its corresponding published European Patent Application no. EP 974,936, as well as in U.S. patent application Ser. No. 09/357,559 filed on Jul. 22, 1999, the disclosures of which are also incorporated herein in their entirety by reference. As indicated in these applications, location and electrical activity is preferably initially measured at about 10 to about 20 points on the interior surface of the heart. These data points are then generally sufficient to generate a preliminary reconstruction or map of the cardiac surface to a satisfactory quality. The preliminary map may be combined with data taken at additional points in order to generate a more comprehensive map of the heart's electrical activity. The detailed map so obtained may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer the motion characteristics such as the contractility of the tissue. As disclosed in U.S. Pat. Nos. 5,738,096 and 6,066,094, incorporated herein in depicting such motion characteristics may be constructed when the trajectory information is sampled at a sufficient number of points in the heart. A high quality preliminary map of motion characteristics is dependent on acquiring a sufficient number of points representatively spaced about the heart chamber volume.

In constructing these preliminary maps, it is desirable that the data are sampled at points sufficiently spaced to outline the entire volume of the chamber under study. If the preliminary map adequately outlines the heart volume, acquisition of additional points will generally enable the detailed reconstruction to permit accurate diagnosis and treatment. Occasionally however, incomplete sampling, as, for example, by localizing the sample points to only a portion of the heart volume, will result in the generation of an incomplete map. Further sampling may lead to a more detailed map of the partial cardiac volume, but this may be inadequate for proper diagnosis and treatment.

In creating maps of the heart using the above-referenced systems, the initial data points for the preliminary reconstruction are generally acquired under the guidance of an imaging modality such as fluoroscopy that permits the cardiologist to observe the placement of the catheter tip within the heart chamber. Once the preliminary map is generated, subsequent points may then be acquired under the guidance of the preliminary map and a location system based on, for example, electromagnetic or acoustic sensors. Unfortunately, unassisted fluoroscopy provides relatively poor visualization of topographical features within the heart. While contrast-assisted fluoroscopy, in which a contrast agent is injected into the heart chamber under examination, significantly improves the observation of topography, the contrast agent obscures the observation of the catheter tip. Thus, fluoroscopy is insufficient to properly guide the cardiologist to the points on the interior of the heart necessary for the generation of a preliminary map of the electrical activity that roughly encompasses the complete heart volume. The potentially harmful effects of the contrast agent and of ionizing radiation to the patient also limit the amount of data that can be collected under fluoroscopy.

Electrical activity at a point in the heart is typically measured by advancing a catheter containing an electrical sensor (an electrode) at or near its distal tip to that point in the heart, firmly contacting the tissue with the electrode and acquiring data at that point. Alternatively, electrical activity may be measured with catheters containing multiple electrodes. In the case of catheters with multiple electrodes, one or more electrodes are generally present at the catheter tip and other electrodes may be present along the catheter body.

It is generally important to maintain good electrical contact between the electrodes and the tissue in order to obtain a reliable and stable electrical reading. Fluoroscopy produces images that are lacking in topographical detail. Accordingly, in taking measurements under the guidance of this imaging modality, the catheter tip may not actually be in effective contact with the tissue. Alternatively, it may be possible to bruise the intracardial tissue by excessive pressure of the catheter tip against the tissue while making such measurements.

PCT application WO 98/35720 discloses an x-ray guided surgical location system with extended mapping volume. The application does not teach or suggest navigation of a catheter tip for the purpose of mapping a chamber of a heart guided by topological information contained in acquired images of the chamber.

U.S. Pat. No. 5,391,199 discloses an apparatus and method for treating cardiac arrhythmias. The method of the '199 patent comprises obtaining a perspective image of the organ to be mapped; advancing one or more catheters to sites adjacent to or within the organ; sensing the location of each of the catheter's distal tips with a non-ionizing field; sensing local information of the organ; processing the local information to create one or more data points; and superimposing the one or more data points on the perspective image of the organ or structure. The '199 patent does not teach or suggest the registration of the image with a positional frame of reference of a position sensor contained in or proximate to the catheter tip. Furthermore, the '199 patent does not teach or suggest navigating the catheter tip under the guidance of topological information contained in acquired images of the chamber.

U.S. Pat. No. 5,433,198 discloses an apparatus and method for cardiac ablation. The apparatus and method of the '198 patent includes a multi-electrode catheter introduced percutaneously into a subject's heart and deployable adjacent to various endocardial sites. The electrodes are connectable to a mapping unit, an ablation power unit and a pacing unit, all of which are under computer control. Intracardiac electrogram signals emanated from a tachycardia site of origin are detectable by the electrodes. Their arrival times are processed to generate various visual maps to purportedly provide real-time guidance for steering the catheter to the tachycardia site of origin. In one aspect, the apparatus of the '198 patent also includes a physical imaging system which is capable of providing different imaged physical views of the catheter and the heart. These physical views are said to be incorporated into the various visual maps to provide a more physical representation. The '198 patent does not disclose or suggest the use of a catheter having a sensor which provides three-dimensional position information of the catheter tip in a positional frame of reference, nor does it disclose or suggest registering chamber images with said frame of reference.

U.S. Pat. No. 6,052,618 discloses a device for mapping electrical activity in the heart. The device of the '618 patent has an imaging unit, such as a fluoroscopic imaging unit, for generating a physical in vivo image of a patient's heart as an anatomical reference image; an electrode catheter with at least one electrode for sensing intracardiac electrical activity in a patient's heart; and signal processing equipment for determining activation times from sensed electrical activity at different points in the heart. The device of the '618 patent further includes means for generating a graphic image showing the activation times at different points in the heart and superimposing this graphic image onto the anatomical image. The '618 patent does not disclose or suggest the use of a catheter having a sensor which provides three-dimensional position information of the catheter tip in a positional frame of reference, nor does it disclose or suggest registering chamber images with said frame of reference. Furthermore, as stated at column 3 lines 34–38 of the '618 patent, "In this type of image, the heart appears, at best, as a pale shadow. The heart is not shown at all in these figures. The body parts seen most clearly in the radiograph are skeletal parts, such as spinal vertebrae and ribs." Thus, the '618 patent does not teach or suggest the use of images containing topological information suitable for guiding the navigation of the catheter tip.

SUMMARY OF THE INVENTION

The present invention is directed to a method for intracardially mapping a condition of a chamber of a heart of a subject. The method of the invention is preferably applied to the mapping of an electrical, mechanical or electromechanical condition of the heart chamber. While the method may be applied to any of the heart's chambers, it is especially useful for the mapping of the left ventricle. The mapping is conducted with a mapping catheter having a distal tip. The catheter distal tip has at least one sensor contained therein or proximate thereto that is capable of sensing condition information of the chamber and providing three-dimensional position information of the catheter tip in a positional frame of reference. The method of the invention involves acquiring a first image of the chamber taken from a first projection and a second image of the chamber taken from a second projection wherein the second projection is different from the first projection. The two projections are preferably separated by an angle of between about 75 degrees to about 105 degrees, and, more preferably, the two projections are separated by an angle of about 90 degrees. The first and second images are taken from two perspectives such as a left anterior oblique (LAO) and a right anterior oblique(RAO) projection. The two images are preferably contrast-assisted fluoroscopic images that depict the chamber at the same phase in the cardiac cycle, preferably, at end-diastole. Both the first and second chamber images contain topological information of the chamber that include the chamber contour. The method further comprises registering the first image and the second image with the positional frame of reference. The distal tip of the mapping catheter is advanced into the chamber to an acquisition point where condition information and position information are to be acquired with the at least one sensor. The catheter tip is navigated to the acquisition point in the chamber guided by topological information contained in or derived from the first and second images. The topological information used to guide the navigation of the catheter is preferably a reconstruction of the chamber, such as a three-dimensional reconstruction derived from the topological information contained in the chamber images. After the condition and position information are acquired at the first acquisition point, the catheter tip is similarly navigated to additional acquisition points where additional condition and position information are acquired. The acquisition points are sufficient in number and spacing throughout the chamber to permit the generation of a map of the condition in the chamber, which is preferably created from the acquired condition and position information.

In one embodiment, the at least one sensor comprises a position sensor capable of providing both three-dimensional position information as well as mechanical condition information. In another embodiment, the at least one sensor comprises a position sensor capable of providing three-dimensional position information and an electrode for sensing electrical information. The at least one sensor preferably comprises an electromagnetic sensor that generates signals responsive to the strength of a magnetic field generated by magnetic field radiators external to the patient wherein the signal intensity is indicative of the three-dimensional position of the sensor in the frame of reference.

The method of mapping a chamber of the heart of the invention further preferably comprises acquiring an image of a scaling object from each of the first and the second projections. The images of the scaling object are used to scale the images of the heart chamber. The method also preferably further comprises affixing a registration position sensor to the patient prior to the acquisition of the first and second images of the chamber. The registration position sensor is affixed to the patient so that an image of the registration position sensor is included in the chamber images. The three-dimensional position coordinates of the registration position sensor are determined and used to register the images of the chamber in the frame of reference.

In another embodiment, the invention is directed to a method for intracardially mapping a condition of a chamber of a heart of a subject. The method of the invention is preferably applied to the mapping of an electrical, mechanical or electromechanical condition of the heart chamber. While the method may be applied to any of the heart's chambers, it is especially useful for the mapping of the left ventricle. The mapping is conducted with a mapping catheter having a distal tip. The catheter distal tip has at least one sensor contained therein or proximate thereto that is capable of sensing condition information of the chamber and providing three-dimensional position information of the catheter tip in a positional frame of reference. The catheter distal tip is advanced into the chamber and the catheter tip is navigated to an acquisition point in the chamber. Navigation of the catheter tip is guided by a reconstruction, preferably a three-dimensional reconstruction of topological features of the chamber registered in the positional frame of reference. After the condition and position information are acquired at the first acquisition point, the catheter tip is similarly navigated to additional acquisition points where additional condition and position information are acquired. The acquisition points are sufficient in number and spacing throughout the chamber to permit the generation of a map of the condition in the chamber, which is preferably created from the acquired condition and position information.

The reconstruction of the chamber used to guide the navigation of the catheter tip is preferably based on a first image of the chamber taken from a first projection and a second image of the chamber taken from a second projection. The first projection and the second projection are preferably separated by an angle of about 75 degrees to about 105 degrees, and more preferably, by an angle of about 90 degrees. The first image and the second image are preferably taken from an LAO projection and an RAO projection. Each of the first and second images contain topological information of the chamber. The topological information contained in the images preferably comprises the chamber contour. The first and second chamber images are preferably contrast-assisted fluoroscopic images. The images preferably depict the chamber at the same phase of the cardiac cycle, preferably at end-diastole.

In one embodiment, the at least one sensor comprises a position sensor capable of providing both three-dimensional position information as well as mechanical condition information. In another embodiment, the at least one sensor comprises a position sensor capable of providing three-dimensional position information and an electrode for sensing electrical information. The at least one sensor preferably comprises an electromagnetic sensor that generates signals responsive to the strength of a magnetic field generated by magnetic field radiators external to the patient, the signal intensity being indicative of the three-dimensional position of the sensor in the frame of reference.

The method of mapping a chamber of a heart of the invention preferably further comprises acquiring an image of a scaling object from each of the first and second projections. The images of the scaling object are used to scale the chamber images. The method of the invention preferably further comprises affixing a registration position sensor to the patient prior to acquisition of the first and second chamber images. The registration position sensor is affixed to the patient so that an image of the registration position sensor is included in the chamber images. The three-dimensional position coordinates of the registration position sensor are determined and used to register the images of the chamber in the frame of reference.

Another aspect of the invention is directed to an apparatus for intracardially mapping a condition of a chamber of a heart. The apparatus of the invention comprises a mapping catheter having a distal tip. The catheter distal tip has at least one sensor contained therein or proximate thereto. The at least one sensor is capable of sensing condition information of the chamber and provides three-dimensional position information of the catheter tip in a frame of reference. The apparatus of the invention further comprises means for registering a plurality of images of the chamber with the positional frame of reference. The chamber images are taken from a plurality of projections relative to the chamber and contain topological information of the chamber. The apparatus of the invention also comprises signal processing circuits for acquiring condition information and position information at a plurality of acquisition points in the chamber with the at least one sensor wherein the points are sufficient in number and spacing throughout the chamber to permit the generation of a map of the condition in the chamber.

The at least one sensor contained in or proximate to the catheter distal tip preferably comprises a position sensor capable of providing three-dimensional position information and an electrode for sensing electrical information. More preferably, the at least one sensor comprises an electromagnetic sensor that generates signals responsive to the strength of a magnetic field generated by magnetic field radiators external to the patient. The intensity of the signals generated by the sensor is indicative of the three-dimensional position of the sensor in the frame of reference.

The apparatus for mapping a chamber of a heart of the invention preferably further comprises a scaling object. The apparatus also preferably further comprises a registration position sensor to register the images with the frame of reference.

The apparatus of the invention also preferably further comprises image-processing circuits for constructing a reconstruction, preferably a three-dimensional reconstruction of the chamber from topological information contained in the chamber images. The apparatus also preferably further comprises circuits for mapping the condition of the chamber using the condition and position information acquired with the at least one sensor.

In another embodiment, the invention is directed to an apparatus for intracardially mapping a condition of a chamber of a heart of a subject. The apparatus of the invention comprises a mapping catheter having a distal tip. The catheter distal tip has at least one sensor contained therein or proximate thereto. The at least one sensor is capable of sensing condition information of the chamber and provides three-dimensional position information of the catheter tip in a frame of reference. The apparatus further comprises image processing circuits for constructing a topological reconstruction, preferably, a three-dimensional reconstruction, of the chamber in the frame of reference, as well as signal processing circuits for acquiring condition information and position information at a plurality of acquisition points in the chamber with the at least one sensor. Condition and position information is acquired at points sufficient in number and spacing throughout the chamber to permit the generation of a map of the condition in the chamber.

The image processing circuits used in the apparatus of the invention preferably construct the topological reconstruction from a plurality of images of the chamber. The images are taken from a plurality of projections relative to the chamber wherein each image contains topological information of the chamber.

The at least one sensor contained in or proximate to the catheter distal tip preferably comprises a position sensor capable of providing three-dimensional position information and an electrode for sensing electrical information. More preferably, the at least one sensor comprises an electromagnetic sensor that generates signals responsive to the strength of a magnetic field generated by magnetic field radiators external to the patient. The intensity of the signals generated by the electromagnetic sensor is indicative of the three-dimensional position of the sensor in the frame of reference.

The apparatus of the invention preferably further comprises a scaling object. The apparatus also preferably further comprises a registration position sensor to register the images with the frame of reference.

The features and advantages of the invention will be more readily apparent from the detailed description set forth below, taken in conjunction with the accompanying drawings.

DETAILED DESCRIPTION OF PREFERRED EMBODIMENTS

The present invention is directed to methods and apparatus for intracardially surveying a condition of a chamber of a heart of a subject. The method and apparatus of the invention are amenable to surveying the condition of any of the heart's chambers, but they are particularly useful in surveying the condition of the left ventricle of the heart.

The method and apparatus of the invention may be used to survey one or more conditions or properties of the tissue comprising the chambers of the heart. As used herein, the term "condition" refers to either a scalar or a vector quantity, and may comprise, for example, an electrical property, a temperature, a pressure, a pH, a measure of local heart movement or any other condition or combination thereof. The method and apparatus of the invention are especially useful for surveying electrical properties of a heart chamber, including but not limited to voltage, impedance, conduction velocity and local activation time (LAT).

As used herein, the term "survey" refers to the collection of data as to the condition of the chamber at representative points throughout the chamber. The condition information may be collected individually, or it may be collected together with position information so that each data point would reflect the condition information at a given three-dimensional coordinate within the chamber. If many points are sampled during the survey, the survey may be useful in providing a comprehensive representation of the condition information throughout the heart chamber. Alternatively, the survey may be preliminary, in which relatively few points are sampled around the chamber. However, even in the case of a preliminary survey, if the points are sufficient in number and in distribution around the chamber, the resultant data may be used for establishing a "boundary map" of the chamber, the detailed state of which may be determined using subsequent more comprehensive sampling. The method and apparatus of the invention are especially useful for conducting such preliminary surveys.

Figure 15:
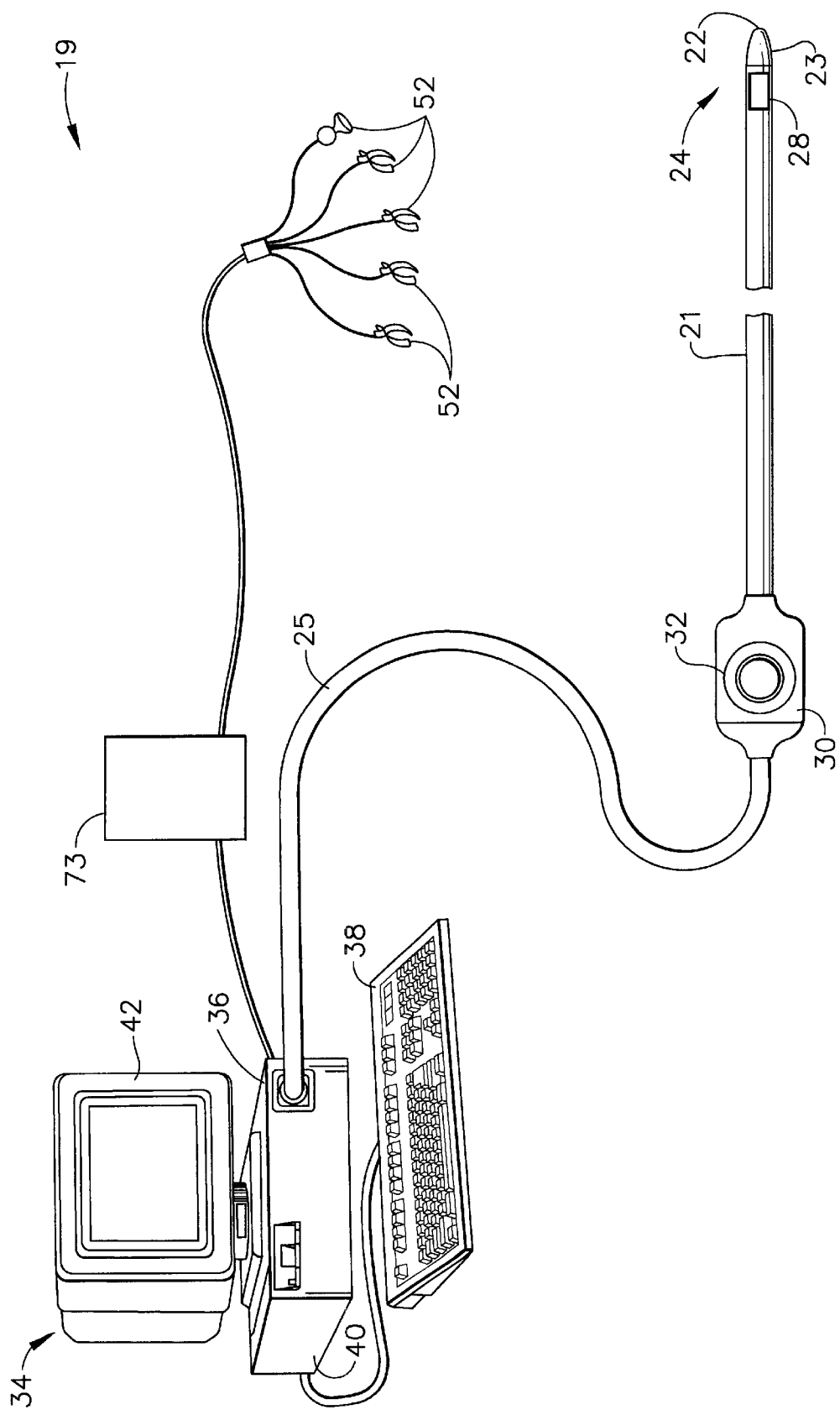
FIG. 15 shows some elements of a position sensor location system for performing the method of the invention.

FIG. 15 shows elements of a preferred position sensor location system 19 for carrying out the methods of the invention. The apparatus includes catheter 21 for insertion into the human body. Distal end 24 of catheter 21 includes a functional portion 23 for performing diagnostic and/or therapeutic functions, adjacent to distal tip 22. Functional portion 23 preferably comprises electrodes or sensors for performing electrophysiological measurements, as described, for example, in U.S. Pat. No. 5,391,199 or in PCT application WO97/24983, which are incorporated herein by reference. Alternatively or additionally, functional portion 23 may include other diagnostic apparatus for recording parameter values at points within the body. Functional portion 23 may also include therapeutic apparatus as known in the art.

Distal end 22 preferably includes a position sensor 28 that generates signals used to determine the position, and, preferably, the orientation of the catheter within the body. Position sensor 28 is preferably adjacent to functional portion 23 in a fixed relation with tip 22. Position sensor 28 preferably comprises three coils, such as described in PCT application WO96/05768, which is incorporated herein in its entirety by reference. The position sensor 28 enables continuous generation of six dimensions of position and orientation information with respect to externally applied magnetic fields. Alternatively, position sensor 28 may comprise other position and/or coordinate sensors as described in U.S. Pat. No. 5,391,199, U.S. Pat. No. 5,443,489 and PCT application WO94/04938 which are incorporated herein by reference. Further, tip 22 may be coated with an opaque marking material to visualize the tip under an imaging apparatus such as a fluoroscope.

Catheter 21 preferably includes a handle 30, having controls 32 that are used to steer distal end 24 of catheter 21 in a desired direction. Catheter 21 preferably comprises a steering mechanism in distal end 24 as is known in the art to facilitate repositioning of tip 22.

Catheter 21 is coupled via an extension cable 25 to a console 34 which enables the user to observe and regulate the function of catheter 21. Console 34 preferably includes a computer 36, keyboard 38, signal-processing circuitry 40, which are typically inside computer 36, and display 42. Signal processing circuits 40 typically receive, amplify, filter and digitize signals from catheter 21, including signals from position sensor 28 and functional portion 23, whereupon these digitized signals are used by computer 36 to compute the condition information and the position and/or orientation of catheter tip 22. Alternatively, appropriate circuitry may be associated with catheter 21 itself so that circuits 40 receive signals that are already amplified, filtered and/or digitized. Preferably, computer 36 includes a memory for storing position and condition information. Computer 36 also comprises image-processing circuits for capturing images from an imaging modality either using a video or a DICOM protocol interface, and for rapidly extracting topographical information from the images. Image processing circuits contained in computer 36 also register the images with the position sensor location system frame of reference and calculate the chamber reconstruction from the chamber topological information contained in the chamber images. Computer 36 preferably further comprises dedicated graphics circuitry for displaying the chamber reconstruction and for superposition of topographical images with other images displaying catheter tip 22 in the body. Images containing contour information, images showing the catheter tip 22, images showing chamber reconstruction 160 (FIG. 14) and superpositions of these images are displayed on display 42. Preferably, the computer is equipped to receive body surface ECG signals from ECG monitor 73 that is connected to a plurality of ECG body surface leads 52. Alternatively, ECG monitoring may also be conducted directly by circuits 40.

Figure 16:
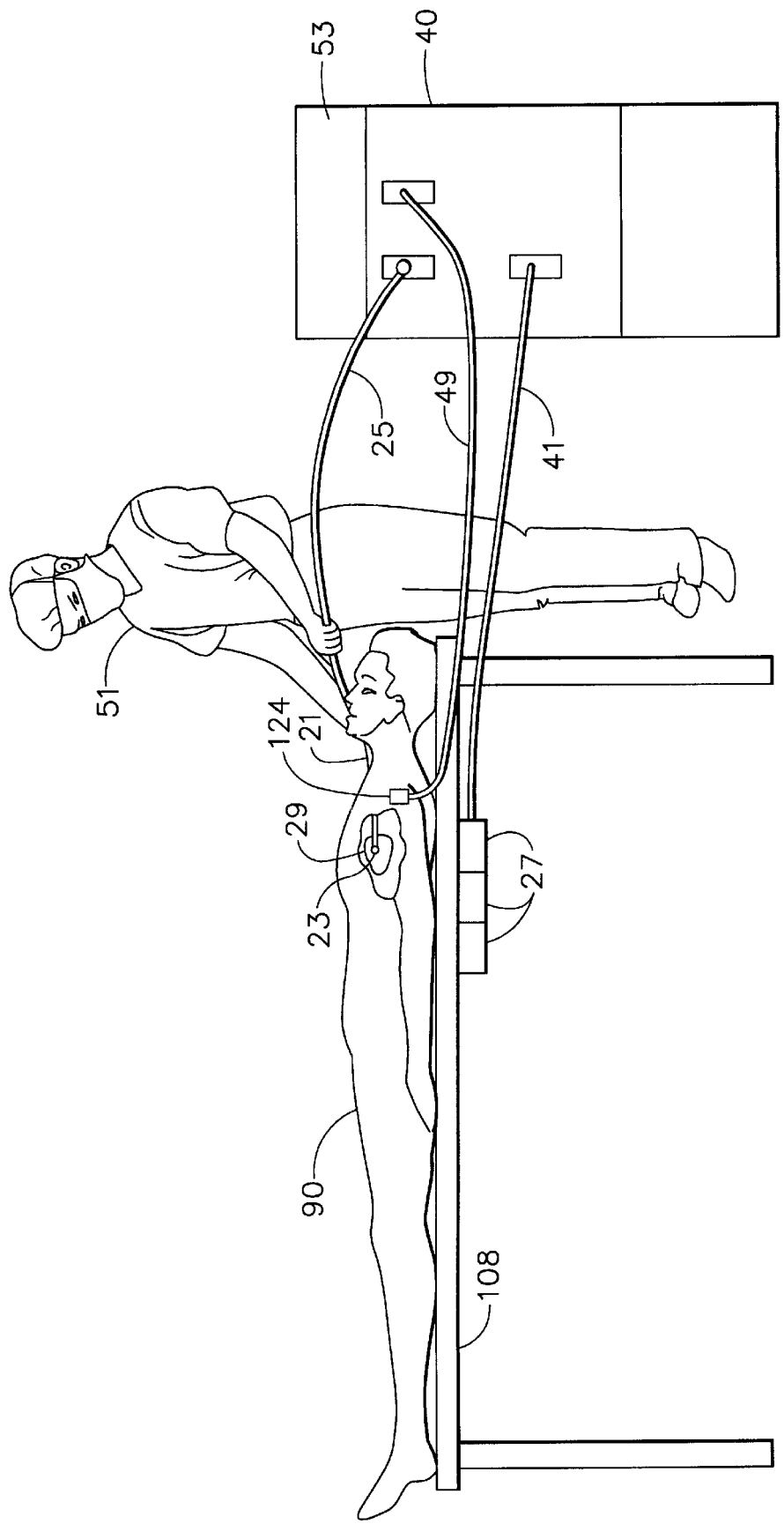
FIG. 16 shows additional elements of a position sensor location system for performing the method of the invention.

Additional elements of the position sensor location system used in connection with the present invention are illustrated schematically in FIG. 16. A physician 51 inserts catheter 21 through an incision in the vasculature, e.g., using an intravascular approach, into a chamber of a heart 29 of a patient 110, so that an electrode contained in functional portion 23 of catheter distal tip 22 and position sensor 28 are inside the chamber. In accordance with an exemplary position sensor described in PCT patent application number WO 96/05768, filed Jan. 24, 1995, and in U.S. Pat. No. 5,391,199, which are assigned to the assignee of the present application and whose disclosures are incorporated herein in their entirety by reference, sensor 28 generates signals in response to externally applied magnetic fields generated by electromagnetic field generator coils 27 fixed to operating table 108 in proximity to patient 90. The magnitude of the signals generated by sensor 28 depends on the position and orientation of the sensor in the applied magnetic field. Field generator coils 27 are connected via cable 41 to driver circuits which are part of signal processing circuits 40. Circuits 40 control the operation of the generator coils 27 and the overall position sensor location system.

Alternatively, the system of the invention may employ field generator coils in the catheter and sensors external to the patient.

The method of the invention also uses a registration position sensor (reference sensor) 124 affixed to the patient during the acquisition of images of the heart chamber. Registration position sensor 124 is connected to circuits 40 via cable 49. The two dimensional coordinates of registration position sensor 124 in the images and the three dimensional coordinates of sensor 124 in the frame of reference of the position sensor location system are used to register the images with the position sensor location system frame of reference.

While the system and method of the invention are described herein with reference to electromagnetic sensors, any other location sensor that provides three-dimensional position information and, optionally, orientation information, may be used in the practice of the invention. Illustrative sensors that are also useful include acoustic sensors and magnetic sensors. For example, acoustic sensors of the type disclosed in U.S. Pat. No. 5,409,000 and in PCT application WO 99/05971, the disclosures of which are incorporated herein in their entirety by reference, may be used in accordance with the system and method of the invention.

As disclosed in U.S. Pat. No. 5, 391,199, mapping the electrical activity of the heart is performed by positioning the distal tip 22 of catheter 21 at a site within the heart, sensing location and electrical information at the site, processing the sensed location and electrical information at the site to create a data point, and repeating these steps a sufficient number of times to create a map of the heart's electrical pathways. For an accurate map of the chamber electrical activity, location and electrical data are preferably sensed when an electrode at distal tip 22 is in contact with the cardiac wall at each site.

Having identified a lesion responsible for an aberrant electrical pathway from the resultant electrical map of the heart chamber, the aberrant pathway may be treated by ablating the cardiac surface at the lesion site. As shown in FIG. 16, ablation is typically performed by supplying RF energy to the site from ablation power source 53 via circuits 40 and cable 25 to an electrode contained at distal tip 22 of catheter 21. Alternatively, therapeutics may be delivered to the site of the lesion using a delivery catheter that has position sensing capability as described for example in copending U.S. patent applications Ser. Nos. 09/19,453 and 09/379,540, the disclosures of which are hereby incorporated herein by reference.

In this embodiment of the invention, the chamber of the heart is mapped with the aid of a mapping catheter 21 having distal tip 22. The catheter has at least one sensor in or proximate to the catheter distal tip 22, preferably in a positionally fixed relationship thereto. The at least one sensor is capable of sensing condition information of the chamber, and also provides three-dimensional position information of the catheter tip in a positional frame of reference.

Preferably, the three-dimensional position information is provided by an electromagnetic position sensor 28 of the type hereinabove described. The electromagnetic position sensor 28 generates signals responsive to the strength of a magnetic field generated by magnetic field radiators 27 external to the patient, the signals being indicative of the three-dimensional position of the sensor in the magnetic field.

The three-dimensional coordinates of the mapping catheter position sensor 28 are usually determined relative to the position of the reference sensor 124. The reference sensor 124 is also preferably an electromagnetic sensor that operates according to the same principles as the position sensor 28 in the mapping catheter 21. The reference sensor 124 may be positioned external to the patient, for example, as part of an adhesive patch applied to the patient's skin as shown in FIG. 16. Alternatively, the reference sensor 124 may be positioned internal to the patient, for example, as a component of a reference catheter that is positioned at a particular point in the heart of the patient during the mapping procedure. Thus, the position sensor 28 in the mapping catheter 21 provides the three-dimensional coordinates of the mapping catheter tip 22 in the frame of reference of the position sensor location system relative to the reference position sensor 124.

As indicated hereinabove, the method of the invention is directed to mapping a condition such as a mechanical and/or an electrical condition of a heart chamber. Mechanical properties of the heart may be mapped, for example, by measuring the extent of local heart movement of the tissue as a function of location within the heart. Local heart movement at a particular location may be assessed by positioning the catheter tip 22 at the location and measuring the coordinates of the catheter tip 22 during various phases of the cardiac cycle. In this case, the position sensor 28 described hereinabove may function to supply both the three-dimensional position information as well as the mechanical condition information.

Electrical information is typically measured by an electrode contained at the catheter tip. In the acquisition of information for an electrical map of the heart chamber, the catheter 21 includes at least two sensors; a position sensor 28 for sensing the three-dimensional position of the catheter tip 22 as well as an electrode 23 (condition sensor) for sensing electrical information.

The invention will now be described in terms of a method and apparatus for measuring the electrical properties of the heart. However, it will be understood that using the appropriate sensors, the method is equally applicable to measuring any of the above-enumerated conditions.

Figure 2:
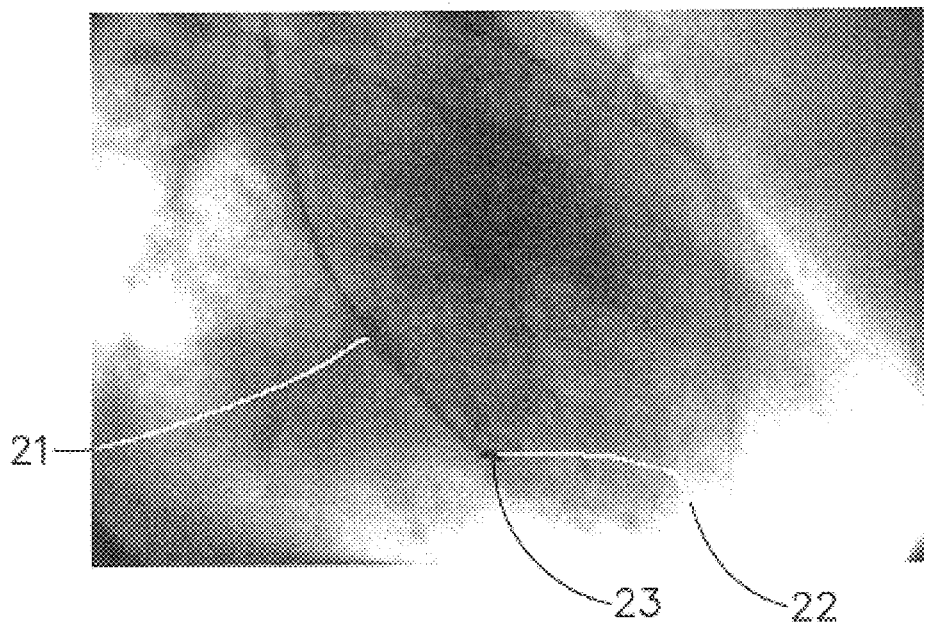
FIG. 2 is a fluoroscopic image of a catheter located in the heart of FIG. 1 taken from the RAO projection.

As shown in FIG. 2, the catheter 21 has one or more electrical sensors 23 at distal tip 22 to measure conditions of the heart. The condition of the heart chamber is measured by the one or more condition sensors 23 (functional portion) contained at or proximate the distal tip 22 of catheter 21 that is advanced into the chamber being surveyed. In the case where catheter 21 has a single condition sensor 23, the condition sensor 23 is preferably contained at the catheter distal tip 22. Using such a single condition sensor catheter 21 in the method of the invention, the condition information of the tissue in the chamber is sensed and acquired on a point-by-basis. The condition at any point in the chamber is determined by advancing the catheter 21 to that point, preferably contacting the tissue at that point with the electrical sensor 23 contained at the catheter distal tip 22, and acquiring the condition information over some time period. Typically, the data at each point are acquired as a function of time for one or more cardiac cycles. The data are then stored in computer memory for future use, as, for example, in the construction of a two-dimensional or a three-dimensional map that graphically depicts the measured condition over all or a portion of the chamber.

Catheter 21 used in the method and apparatus of the invention may have more than one condition sensor 23 contained therein. Catheters containing multiple sensors that may be useful in characterizing the electrical properties the heart tissue are described, for example in U.S. Pat. Nos. 5,409,000; 5,588,432; 5,931,863; 5,931,835; and 5,921,924, and in U.S. patent application Ser. No. 09/506,766 which are hereby incorporated herein in their entirety by reference. The use of multi-sensor catheters in the method and apparatus of the invention permit the simultaneous measurement of condition information at multiple points in the heart chamber, which can potentially decrease the time required for assessing the overall condition of the heart chamber.

As best illustrated in FIG. 15, the catheter 21 used in the method and apparatus of the invention preferably further comprises one or more position sensors 28 proximate to distal tip 22 that are used to accurately measure the position and/or the orientation of the catheter tip 22 in the body, particularly, in the heart of the subject. The position sensor 28 may, for example, operate by sensing or transmitting acoustic, magnetic or electromagnetic fields. An electromagnetic field sensor is preferred as a position sensor. Preferably, position information is sensed by the position sensors 28 and acquired simultaneous with the sensing of condition information by the condition sensor 23. Catheters having sensors capable of use in measuring both electrical properties of the heart tissue as well as the location of the catheter tip are described for example in U.S. patent application Ser. No. 08/793,371 and in corresponding PCT application WO96/05768, which are hereby incorporated in their entirety by reference. By way of example, the NAVI-STAR® catheter, available from Biosense-Webster, Inc. of Diamond Bar, Calif., is a catheter having both electrical condition and position sensors contained therein that may be useful in practicing the method of the present invention.

The mechanical condition of cardiac tissue may be assessed by measuring the extent of movement of the tissue at a plurality of points on the endocardium. Such movement may be measured by contacting the tissue with a catheter tip 22 containing the position or location sensor 28 at or near its distal tip 22. The extent of tissue movement at each point on the endocardium may be assessed by measuring the distance traversed by a catheter tip 22 in contact with that point throughout a cardiac cycle. A map of the mechanical activity is constructed by collecting such mechanical data at a plurality of points on the cardiac surface wherein each point is characterized by the three-dimensional coordinates of the catheter tip 22 and hence the coordinates of a particular point on the cardiac tissue.

The coordinates of the catheter tip 22 during data acquisition are preferably referenced to a particular point in the cardiac cycle, for example, to the end diastole portion of the cardiac cycle.

When used as described herein to measure the mechanical condition of the cardiac tissue, the location sensor 28 acts not only to determine the location of the tissue at each point, but also as a condition sensor for measurement of mechanical activity. The mechanical condition may be measured alone, or simultaneously with electrical properties of the tissue by electrode 23 (condition sensor) contained at the catheter tip 22.

The catheter 21 used in the method and apparatus of the invention further include means for effecting therapies to the tissue of the heart chamber. For example, endocardial ablation is well known in the art as a therapeutic technique for correcting cardiac arrhythmia. Such therapy may, for example, be effected by delivering radiofrequency energy to the diseased tissue from an RF ablation electrode contained on the catheter distal tip 22.

The method of the invention broadly comprises the following steps:

a) acquiring a first image of the chamber which contains topographical information of the chamber;

b) advancing the distal tip 22 of the catheter 21 into the chamber;

c) acquiring a second image comprising a representation of the catheter distal tip 22 in the chamber;

d) displaying a superposition of topographical information acquired in step (a) with the second image of step (c) to generate a displayed superimposed image comprising representations of the topographical information and the catheter distal tip 22;

e) acquiring condition information at an acquisition point on the chamber with the condition sensor 23, the acquisition point being selected from points on the displayed superimposed image of step (d) proximate the topographical information;

f) repeating step (e) at one or more additional acquisition points, the points being sufficient in number and spacing throughout the chamber to permit the generation of a survey map of the condition in the chamber.

The first step in the method of the invention is to acquire a first image of the heart chamber that contains topographical information. The topographical features typically depicted in the image include the boundary or contour of the interior of the chamber, although other topographical or pathological features may also be depicted. Exemplary imaging modalities that may be used to acquire the first image include single photon emission computerized tomography (SPECT), positron emission tomography (PET), two or three dimensional echo cardiography, magnetic resonance imaging (MRI), computerized tomography (CT) and fluoroscopy. Some of these modalities, e.g., fluoroscopy, may require the injection of a contrast agent into the blood stream or into the chamber to visualize the topographical features of the chamber. Due to the fact that fluoroscopy is a commonly found imaging modality in catheterization laboratories, contrast-assisted fluoroscopy is the preferred imaging modality for acquiring the first image containing topographical information in the method of the invention.

In the case of contrast-assisted fluoroscopy, and perhaps with other imaging modalities, the first image of the chamber containing topographical information is acquired dynamically, i.e., sequential images are acquired after injection of the contrast agent. Sequential images are acquired for at least one and preferably several cardiac cycles. In effect, a multiple frame "moving picture" of the chamber is acquired. In some applications of the method of the invention, it is preferable to select a single frame of the dynamically acquired image for subsequent use in the method of the invention. For these applications, the single frame corresponding to the end-diastole portion of the cardiac cycle is preferred. On the other hand, any other frame may be selected, provided that it is used consistently for extraction of the contour as well as subsequent display of images containing representations of the catheter tip 22.

The end diastole point in the cardiac cycle is the point at which the ventricles are maximally dilated immediately prior to contraction. The frame corresponding to or depicting the chamber in end diastole may be selected by a variety of methods. The frames may be viewed manually and the end diastole frame may be selected as the frame just prior to the ventricular contraction. Alternatively, the end diastole frame may be determined automatically using image-processing techniques. For example, the boundary or contour of the chamber in each frame may be extracted using an algorithm such as snakes. The frame whose contour bounds the maximum area corresponds to the end diastole frame. Alternatively, the frame corresponding to end diastole may be correlated with the body surface electrocardiogram (ECG). Specifically, the end diastole frame may be defined by a particular feature of the QRS wave of the body surface ECG.

Figure 1:
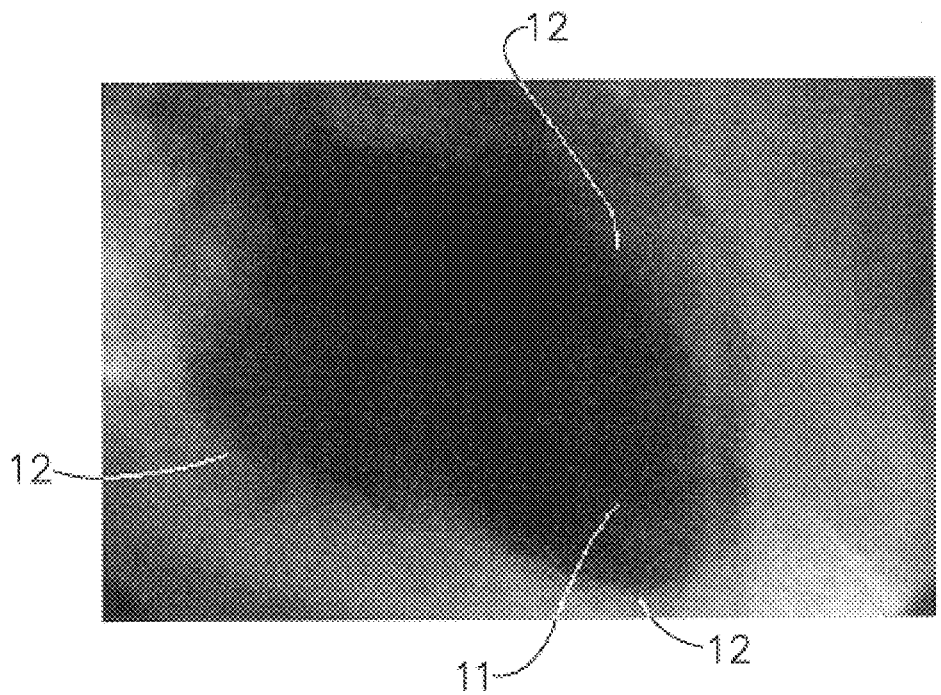
FIG. 1 is an LV-gram image of the left ventricle of a human heart taken from the right anterior oblique (RAO) projection.

In the case in which the left ventricle (LV) is the object of the study, the first image preferably comprises a contrast-assisted fluoroscopy image of the left ventricle, commonly referred to as an LV-gram. An LV-gram image of a human heart showing the ventricle in end diastole, taken from the right anterior oblique (RAO) projection, is shown in FIG. 1. As seen in FIG. 1, the dark area 11 depicts the interior of the left ventricle filled with contrast agent. As the ventricle is completely filled with contrast agent, the topographical features of the ventricle, i.e., the ventricle border or contour 12, is clearly visible in the LV-gram.

After the catheter 21 including condition sensor 23 is advanced into the heart chamber being surveyed, the next step in the method of the invention involves acquiring a second image of the chamber showing the catheter contained therein. The second image may be acquired using one of a variety of imaging modalities, for example, fluoroscopy, echocardiography, MRI or CT. Once again, due to the ubiquitous nature of fluoroscopy in the catheterization laboratory, fluoroscopy is the preferred modality for obtaining the second image in the method of the invention. FIG. 2 shows a fluoroscopic image of the heart of FIG. 1 taken from an RAO projection. The image in FIG. 2 shows the catheter 21 having distal tip 22 with an electrical sensor 23 contained therein. As shown in FIG. 2, however, the non-contrast-assisted fluoroscopic image is not particularly helpful in providing readily discernible visual guidance as to the internal ventricle walls. Furthermore, the fluoroscopic image extends to the epicardium. Accordingly, sampling the condition information at the endocardium under fluoroscopic guidance alone may lead to incomplete sampling in only a portion of the heart chamber and may be less informative in terms of identifying sampling points on the endocardial wall.

The next step in practicing the method of the invention involves displaying a superposition of the topographical information from the first image with the second image comprising a representation of the catheter distal tip 22. In the practice of the method of the invention using dynamically acquired imaging modalities, a variety of superpositions may be performed in displaying the topographical information together with the image showing the catheter tip 22. In the case of contrast-assisted fluoroscopy as the modality for acquiring the first image containing topographical information of the chamber, the contrast-assisted image is dynamically acquired. Accordingly, either a dynamic moving image of the chamber or a static image at a single point in the cardiac cycle may be used in the displayed superposition. Likewise, non-contrast assisted fluoroscopy used to image the catheter tip 22 in the chamber is also dynamically acquired, so that either a dynamic or static image showing the catheter tip 22 may be used.

The purpose of creating the superposed displayed image is two-fold. First, to facilitate the guidance of the catheter tip 22 to the wall of the chamber under examination, and second, to provide a visualization that will permit the cardiologist to acquire data at representative points throughout the chamber. Mere superposition of the images of FIG. 1 and FIG. 2 would be inadequate to serve these purposes, since the dark area of the LV-gram of FIG. 1 showing the interior of the left ventricle would completely obscure the image of the catheter tip 22. Accordingly, it is desirable to extract or derive the contour information from FIG. 1 prior to superposition with the image of FIG. 2.

Figure 3:
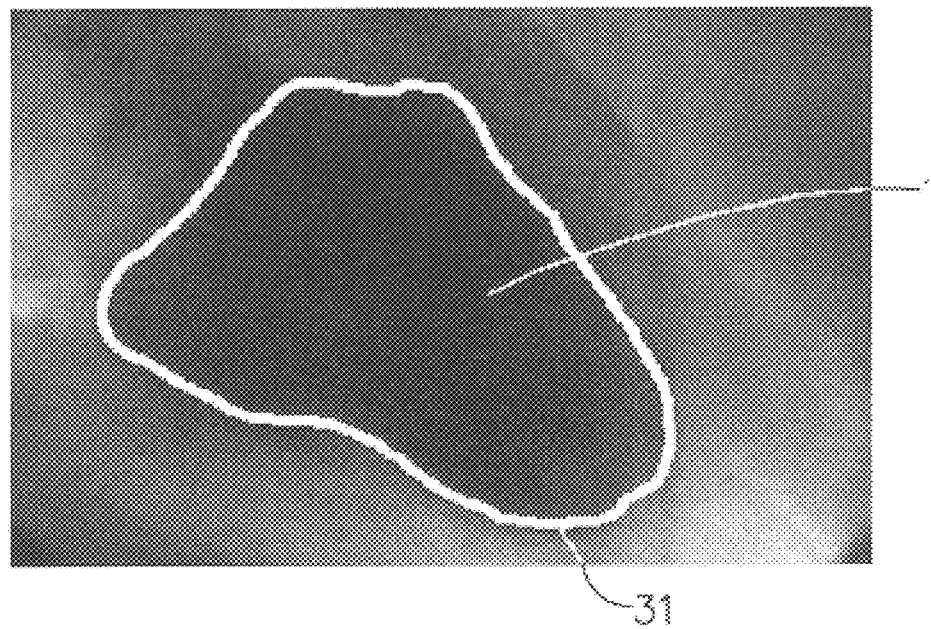
FIG. 3 is the LV-gram of FIG. 1 in which a contour image has been created about the interior of the left ventricle.

FIG. 3 is an LV-gram image of the ventricle shown in FIG. 1 in which contour image 31 has been created about the contour of the interior wall of ventricle 11. The contour image may be created, for example, in one of three ways:

A. Manual Creation of Contour Image—The contrast-assisted image is imported into a drawing program and a continuous contour image is manually traced around the entire ventricle contour using the drawing program drawing tool by manually dragging the mouse pointer or a similar pointing device completely around the contour. Alternatively, the contrast-assisted image may be manually marked at discrete points with the drawing tool and the contour may be interpolated between these points, using splines, for example.

B. Automatic Creation of Contour Image—The contour image is created and extracted automatically using a contour extraction algorithm such as snakes. Snakes were originally proposed as a regularization approach for locating contours (see M. Kass, A. Witkin & D. Terzopoulos, "Snakes: Active Contour Models," Proceedings of First International Conference Vision, 1987, pp. 259–269 and D. Terzopoulos, "Regularization of Inverse Visual Problems Involving Discontinuities," *IEEE Trans. Pat. Anal. Mach. Intell.*, vol. PAMI-8, no. 4, 1986, pp. 413–424).

The contour V may be represented as an ordered set of points, $V=[v_1, v_2, \ldots, v_n]$ wherein each $v_i$ is defined by a pair of (x, y) coordinates. A snake can be either closed or open, depending on whether the end points are connected. In the present invention, we preferably use closed snakes.

We denote two functionals $E_{int}$ and $E_{ext}$. $E_{int}(v_i)$ imposes continuity and smoothness constraints, wherein $E_{ext}(v_i)$ attracts the snake to salient image features, for example, the magnitude of the intensity gradient. We seek to minimize both $E_{int}$ and $E_{ext}$. Minimizing both functionals via the snake then turns the boundary extraction problem into the following energy minimization problem:

$$V_\Lambda = \operatorname*{argmin}_v \sum \lambda_i E_{int}(v_i) + (1 - \lambda_i) E_{ext}(v_i) \quad (1)$$

wherein $\lambda_i \in [0,1]$ is a tradeoff parameter. Setting $\lambda$ to 0 means that we minimize only the $E_{ext}$ component of the equation. Setting $\lambda$ to 1 means minimizing only the $E_{int}$ component. Intermediate $\lambda$s result in a tradeoff of $E_{int}$ vs. $E_{ext}$.

The $\lambda$ parameter may be found empirically or by a parametric selection strategy based on the minimax criterion (see H. Freeman, "Computer processing of Line Drawing Images," *Computer Survey* 6, 1974, pp. 57–98).

In the original formulation, the internal energy $E_{int}$ was defined by the first and the second derivatives along the boundary, giving the snake rubber-sheet and thin-plate like behavior respectively, and is approximated by:

$$E_{int}(v_i) = \|v_i - v_{i-1}\|^2 \|v_{i-1} - 2v_i + v_{i+1}\|^2 \quad (2)$$

Alternatively, $E_{int}(v_i)$ and $E_{ext}(v_i)$ may be defined in different ways, for example, as described by K. F. Lai & R. T. Chin, in "Deformable Contours: Modeling and Extraction", PAMI-17, No. 11, November 1995, pp. 1084–1090.

C. Semiautomatic Creation of Contour Image—In one variation of the semi-automatic method, the physician is presented with a snakes contour for acceptance or rejection. Rejection of the contour results in further processing leading to the presentation of another possible contour. This continues until the physician accepts the contour image. Alternatively, a modified snakes algorithm may be employed which forces the contour image to one or more points pre-selected by the user.

Figure 4:
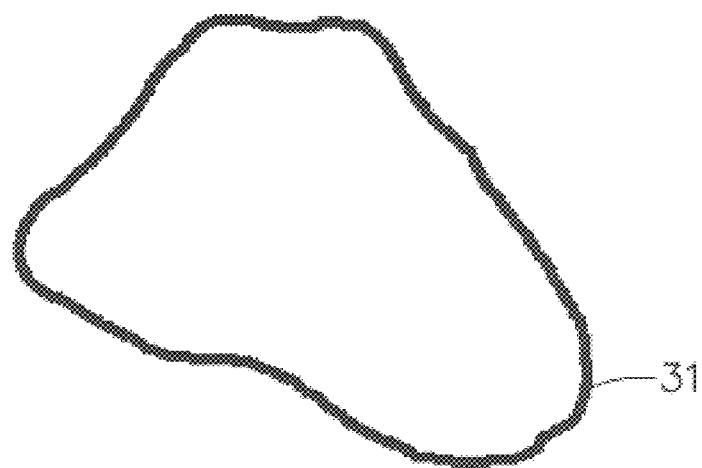
FIG. 4 is the extracted contour image of FIG. 3.

The contour image 31 so produced, extracted from the LV-gram, is shown in FIG. 4. The x, y coordinates of the extracted contour image are preferably stored in computer memory for use in displaying the superposition of topographical information and the image showing the catheter tip 22.

As indicated previously, the contour information and the image showing the catheter tip 22 may be either dynamic or static. The contour 31 and catheter tip 22 information may be superimposed, for example, in the following ways:

A. Static Contour Image On Static Catheter Tip Image

A static contour image is acquired from a dynamic image by one of the hereinabove described methods, e.g., the end diastole frame is acquired by synchronization with the body surface ECG signal. The fluoroscopy image showing the catheter tip 22 is also gated to show the same frame as that selected for the contour image. The superposition of the contour image on the image showing the catheter tip 22 is effected by changing the color or intensity of the pixels corresponding to the stored contour image in the image showing the catheter tip 22.

B. Static Contour Image On Dynamic Catheter Tip Image

The static contour image as hereinabove described is superimposed on a dynamic image of the catheter tip 22 in the heart. In this case, the pixel color or intensity of each frame of the dynamic fluoroscopy image is processed as described above to show the contour image 31 of the chamber 11.

C. Dynamic Contour Image on Dynamic Catheter Tip Image

Rather than selecting a single frame of the contrast-assisted image, the entire sequence is processed to extract the contour of each frame. The stored contours are then synchronized with the live dynamic images of the chamber 11 and catheter tip 22 and each frame of the live images is processed to adjust pixel color or intensity corresponding to the contour at that point in the cardiac cycle.

Figure 5:
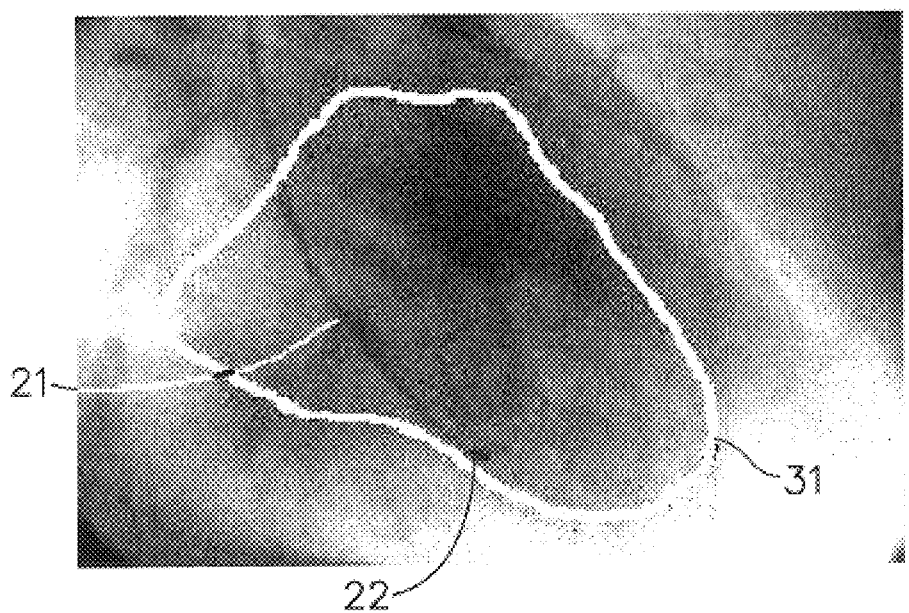
FIG. 5 is a superposition of the contour image of FIG. 4 and the fluoroscopic image of FIG. 2.

The resultant processed images showing the contour and the catheter tip 22 are shown on the display. FIG. 5 is a photograph of the displayed superposition of contour image 31 of FIG. 4 with the fluoroscopic image of FIG. 2 showing a portion of catheter 21 and catheter tip 22.

Since the first image containing the topographical information (FIG. 1) and the second image showing the catheter tip 22 (FIG. 2) were both acquired using the same imaging modality (fluoroscopy) and from the same projection (RAO), contour image 31 in the displayed superimposed image represents points on the interior wall of the chamber 11. Accordingly, in order to acquire condition information concerning the tissue of the chamber, the cardiologist advances the catheter tip 22 under the guidance of the displayed superimposed image of FIG. 5 to an acquisition point shown on the displayed image as being on or proximate to boundary image 31. At this acquisition point, the catheter tip 22 is in contact with or proximate to the chamber wall, and condition information, preferably together with location information, may be acquired. While viewing the displayed superimposed image, the cardiologist may acquire the condition and/or position information by activation of a foot pedal, for example, which instructs the computer to initiate data acquisition. Condition and/or position information are preferably acquired repetitively at each point on the wall of the cardiac chamber for at least one and preferably more than one complete cardiac cycle. Data are preferably acquired at a frequency of at least about 10 per second, more preferably, at a frequency of at least about 20 per second, and most preferably, at a frequency of at least about 50 per second.

After acquiring data at the first acquisition point, the cardiologist acquires subsequent data by advancing the catheter tip 22 to successive points in the chamber, such points being shown in the displayed superimposed image as being on or proximate to the contour image. The total number of data points acquired is a function of the intended purpose of the survey. If only a preliminary survey is being conducted in order to define the boundary of the chamber for another guidance or navigation technique, at least 3 and preferably at least 5 points should be acquired under the guidance of the displayed superimposed image.

As described herein, the first image containing topographical information and the second image containing a representation of the catheter tip 22 are preferably acquired using the same imaging modality, i.e., fluoroscopy. Furthermore, both images are preferably acquired in the same projection, i.e., the images of FIG. 1 and FIG. 2 were both acquired in the RAO projection. Acquiring both images using the same modality and using the same projection is preferred because this eliminates the need to register the images. Alternatively, the first and second images may be acquired using different imaging modalities and/or from different projections. However, such images would require registration during superposition if the displayed superposed image is to serve as a guide for the chamber contour.

To assist the cardiologist in acquiring representative condition information throughout the entire chamber, the method of the invention preferably comprises marking the display at the points at which condition information is acquired. This capability provides the cardiologist with a visual indication of all of the points or sites on the cardiac wall at which information was acquired, and helps guide the cardiologist to sites where sampling is still required.

The display is preferably marked automatically when means such as the foot pedal is activated to initiate data acquisition. The position of the catheter tip 22 in the display is preferably located automatically by the following algorithm. The catheter tip location algorithm is based on the following assumptions:

1) The catheter tip 22 is visualized as dark on the image;
2) The greatest contrast in the displayed superimposed image occurs between the catheter tip 22 and its surroundings; and
3) The size of the catheter tip 22 may be fixed in the analysis of all images.

Figure 8:
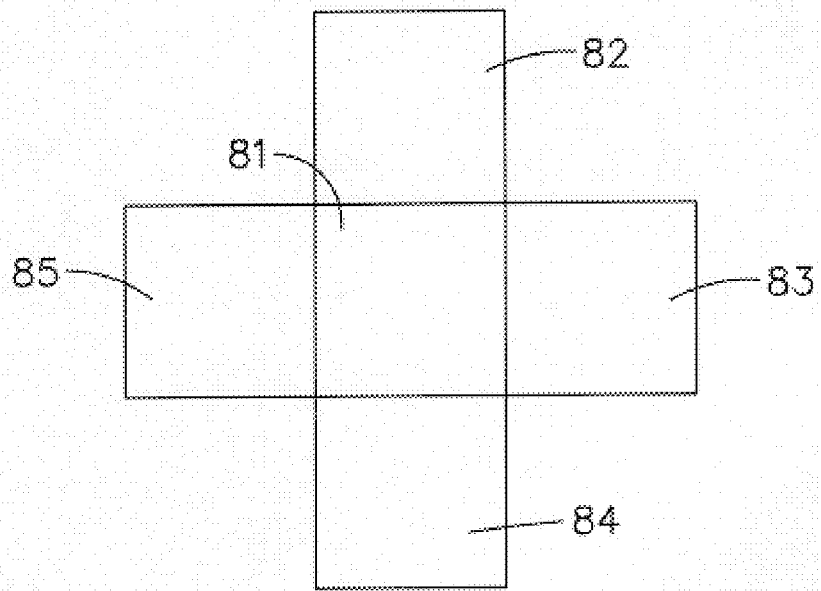
FIG. 8 is a representation of an algorithm used to automatically find a catheter tip in a displayed image.

The algorithm may be understood by reference to FIG. 8, in which the catheter tip 22 is approximated by a fixed geometric shape of a given size, for example square 81 in FIG. 8. Each square is of the same size, between about ten (10) to about twenty (20) pixels. To test whether the catheter tip is visualized in square 81, the average intensity of the pixels comprising square 81 is computed. Similarly, the average intensity is evaluated for the pixels comprising the four squares, 82, 83, 84 and 85 surrounding square 81. The contrast between square 81 and its neighbors 82, 83, 84 and 85 is the difference in average intensity between square 81 and the average intensity of squares 82, 83, 84 and 85. This calculation is iterated about all pixels in the image. The catheter tip location is attributed to the square having the maximum contrast or intensity difference with its surroundings.

Marking the display helps the cardiologist to avoid missing regions of the heart if the objective is to survey the chamber as a whole. Marking the display to indicate the data acquisition sites also permits the cardiologist to return to a visited site, for example, to confirm previously sampled condition information.

The displayed superimposed image may be marked with a geometric symbol for example (e.g., a square, circle, etc.) to depict each point at which condition information was acquired. Alternatively, the display may be marked with a number or color representative of the magnitude of the condition information acquired at that point. The display may be marked, for example, by instructing the computer to mark the display with the position of the catheter tip when the foot pedal, which initiates data acquisition, is activated. Alternatively, the cardiologist may be provided with marking means which allows the selection of which of the acquired points are to be marked on the displayed superimposed image.

Figure 6:
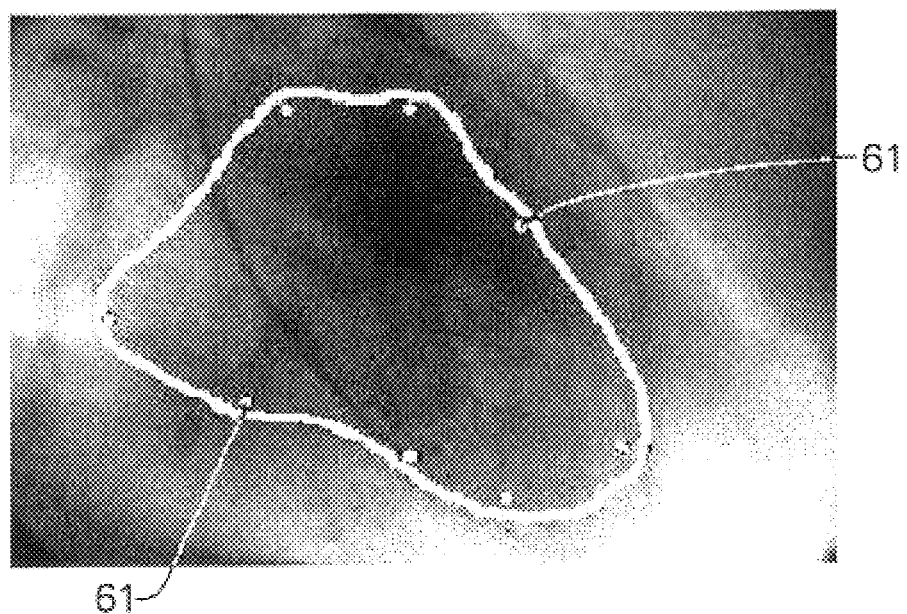
FIG. 6 is the image of FIG. 5 in which the display was marked to indicate points in the chamber from which condition information was acquired.

FIG. 6 depicts the displayed superimposed image of FIG. 5 in which geometric symbols 61 have been marked on the displayed image corresponding to the points in the chamber at which condition information was acquired.

The topographic information used in the method of the invention as heretofore described is two dimensional in nature. Accordingly, the contour image used in the displayed superimposed image only represents points on the interior wall of the heart chamber in a single plane. If the objective of the survey is a more comprehensive characterization of the heart chamber, it may be preferable to perform the method of the invention using images acquired from a plurality of projections. Briefly, the method of the invention in which image and condition information are acquired from two projections using fluoroscopy, the preferred imaging modality, comprises the steps of:

a) acquiring a first, contrast-assisted fluoroscopic image of the chamber, the first, contrast-assisted fluoroscopic image being acquired from a first projection relative to the subject;

b) creating a first contour image of the interior of the chamber from the first contrast-assisted fluoroscopic image;

c) acquiring a second, contrast-assisted fluoroscopic image of the chamber, the second, contrast-assisted fluoroscopic image being acquired from a second projection relative to the subject;

d) creating a second contour image of the interior of the chamber from the second contrast-assisted fluoroscopic image;

e) advancing the distal tip 22 of the catheter 21 into the chamber;

f) acquiring a first non-contrast-assisted fluoroscopic image comprising a representation of the catheter distal tip 22 in the chamber, wherein the first non-contrast-assisted fluoroscopic image is acquired from the first projection relative to the subject;

g) displaying a superposition of the first contour image of step (b) with the first non-contrast-assisted fluoroscopic image of step (f) to generate a first superimposed image;

h) acquiring the condition information at an acquisition point on the chamber with the condition sensor, wherein the acquisition point is selected from points on the first superimposed image of step (g) proximate the first contour image;

i) acquiring a second non-contrast-assisted fluoroscopic image comprising a representation of the catheter distal tip 22 in the chamber, wherein the second non-contrast-assisted fluoroscopic image is acquired from the second projection relative to the subject;

j) displaying a superposition of the second contour image of step (d) with the second non-contrast-assisted fluoroscopic image of step (i) to generate a second superimposed image;

k) acquiring the condition information at an acquisition point on the chamber with the condition sensor, wherein the acquisition point is selected from points on the second superimposed image of step (j) proximate the second contour image;

l) repeating steps (h) and (k) at one or more additional acquisition points, wherein the points are sufficient in number and spacing throughout the chamber to permit the generation of a survey map of the condition in the chamber.

Preferably, all of the data acquired under the guidance of one of the displayed superimposed images is collected before collecting data under the guidance of the second displayed superimposed image.

If only a preliminary survey is being conducted in order to define the boundary of the chamber for another guidance or navigation technique, at least three (3) and preferably at least five (5) points should be acquired under the guidance of each of the displayed superimposed images.

Figure 7:
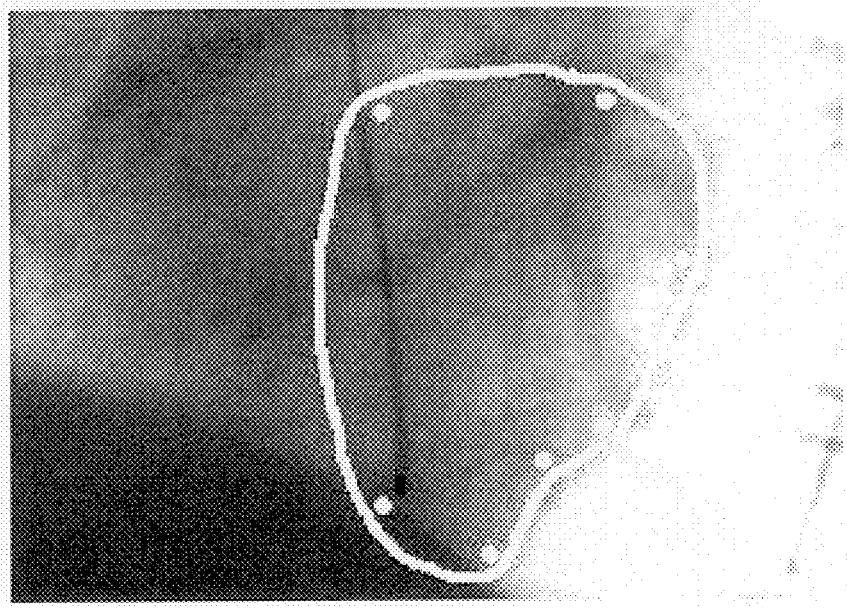
FIG. 7 is equivalent to the image of FIG. 6 taken from the left anterior oblique (LAO) projection.

As hereinabove described, the method of the invention preferably further comprises marking the points 61 on the superimposed image at which the condition information was acquired. FIG. 7 shows a marked superposition of the contour and fluoroscopy images of the left ventricle shown in FIGS. 1–6 in which the images were acquired in a left anterior oblique (LAO) projection. Sampling the condition of the chamber from multiple projections is expected to increase the accuracy of a preliminary map of the heart chamber based on the data.

If the method of the invention is practiced with a catheter containing a sensor for obtaining position information, each data point of condition information obtained via the condition sensor may be accompanied by a three dimensional coordinate of the tissue at which the data point was obtained. The resulting survey data of condition and position information obtained by the practice of the method of the invention is especially useful for the creation of maps, especially 3-dimensional maps of the heart. Methods of creating such maps are disclosed in copending commonly assigned U.S. patent applications Ser. No. 09/122,137 and 09/357,559 filed on Jul. 24, 1998 and Jul. 22, 1999, respectively, which are incorporated herein in their entirety by reference. The method of the invention further optionally comprises the step of creating a map of the condition of the heart based on the position and condition information obtained from the practice of the method of the invention.

In another embodiment, the present invention is directed to methods and apparatus for mapping a chamber of a heart. While useful for any of the heart's chambers, the invention is especially useful for mapping the left ventricle of the heart.

Another embodiment of the method of the invention involves using topological information of the chamber contained in or derived from images acquired from at least two projections. The images are preferably contrast-assisted fluoroscopic images, preferably taken from LAO and RAO projections. As described above, the contrast-assisted fluoroscopic images are acquired dynamically over one or more cardiac cycles. The images taken from each projection preferably depict the chamber at the same phase of the cardiac cycle, preferably at end-diastole. The frames of the fluoroscopic images depicting the chamber in end diastole are selected as described hereinabove.

In some embodiments of the invention, the chamber images are registered with the frame of reference of the position sensor location system. One way of effecting this registration is by:

(1) Obtaining the three-dimensional coordinates of a fiducial object that is visible in the images; and (2) Scaling the images to the position sensor frame of reference.

A convenient fiducial object is a position sensor that is affixed to the patient for purposes of registration of the chamber images. Prior to the acquisition of the images, a registration position sensor 124 (FIG. 16) is affixed to the patient at a location in which it will be visible in each of the chamber images. The registration position sensor 124 may be affixed to the patient either externally or internally. If affixed to the patient externally, it is preferably affixed to the left side of the patient's chest. The registration position sensor 124 is also preferably an electromagnetic sensor of the type hereinabove described. The three-dimensional coordinates of the registration position sensor 124 in the position sensor location system frame of reference are measured and used together with the two-dimensional location of the registration sensor 124 in the chamber images in registering the chamber images in the frame of reference of the position sensor location system.

The other part of the registration procedure involves scaling the chamber images to the position sensor frame of reference. The chamber images are scaled by obtaining images of a scaling object of known dimensions and calculating scaling factors for the chamber images from the images of the scaling object. The scaling object may be positioned either internal to or external to the patient. The scaling object is preferably an x-ray opaque sphere, preferably having a diameter of about 40 mm, taped under the left arm of the patient at approximately the same height as the heart. If the scaling object cannot be seen in the chamber images, separate images of the scaling object should be recorded at the same orientation of the C-arm (projection angle and distance of source and intensifier relative to patient) as the chamber images. The scaling object should preferably occupy the center of the image in order to minimize image distortions. The size of the scaling sphere in the images may be determined automatically by using a region filling algorithm as described in Computer Graphics—Principles and Practice, J. D. Foley, A. van Dam, S. K. Feiner and J. F. Hughes, Addison-Wesley Publishing Company, 1996, pp. 979–986 and by ellipse fitting as described in Digital Image Processing, K. R. Castleman, Prentice Hall, 1996, pp.501–507. The scaling sphere appears as an ellipse in the fluorograms due to different scaling of the fluorograms in the vertical and horizontal directions. Knowing the true size of the scaling object, both vertical and horizontal correction factors may be calculated from the scaling object images. The chamber images are then scaled according to these correction factors.

Figure 9B:
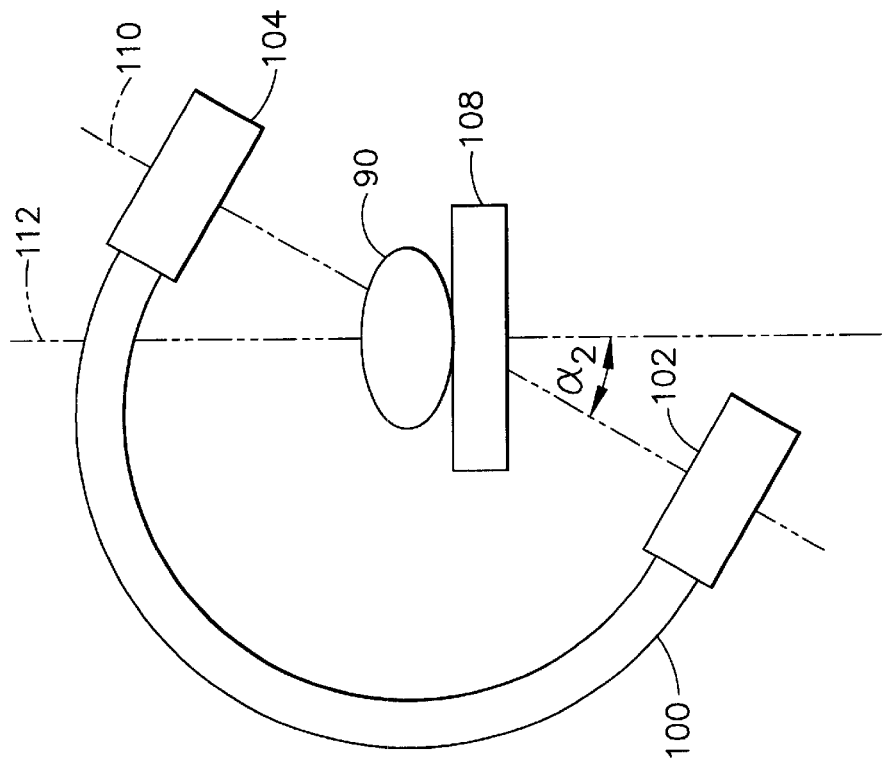
FIG. 9A and FIG. 9B are schematic views of a C-arm taking fluoroscopic images of a chamber of a heart of a patient from the LAO and RAO projections, respectively.
Figure 9A:
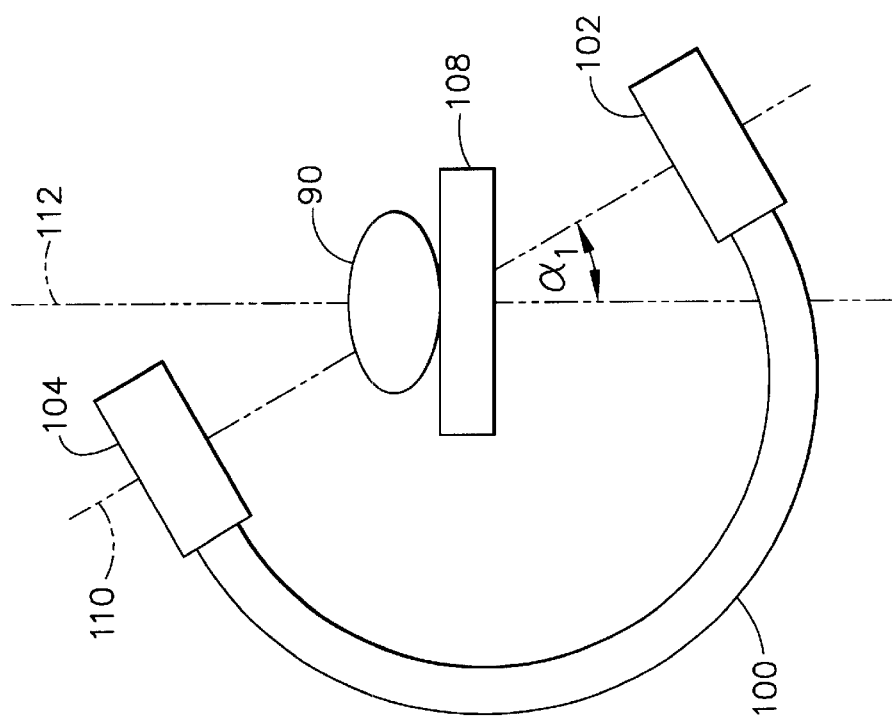

FIGS. 9A and 9B are schematic drawings showing acquisition of the images with a fluoroscope C-arm (fluoroscopic device) 100. The figures show the patient 106 in longitudinal view facing the patient's head. The C-arm 100 connects x-ray source 102 and image intensifier 104. Patient 106 is lying face-up on table 108. FIGS. 9A and 9B depict the acquisition of images in the LAO and RAO projections, respectively. In each of these projections, axis 110 of C-arm 100 creates an angle ($\alpha_1$ and $\alpha_2$ in FIG. 9A and FIG. 9B, respectively) with vertical axis 112. The angle $\alpha_{TOT}$ separating the two projections is the sum of the angles $\alpha_1$ and $\alpha_2$ of the individual projections. Preferably, the two projections are separated by an angle $\alpha_{TOT}$ of between about 75 to about 105 degrees. More preferably, the projections are separated by an angle $\alpha_{TOT}$ of about 90 degrees.

Figure 9C:
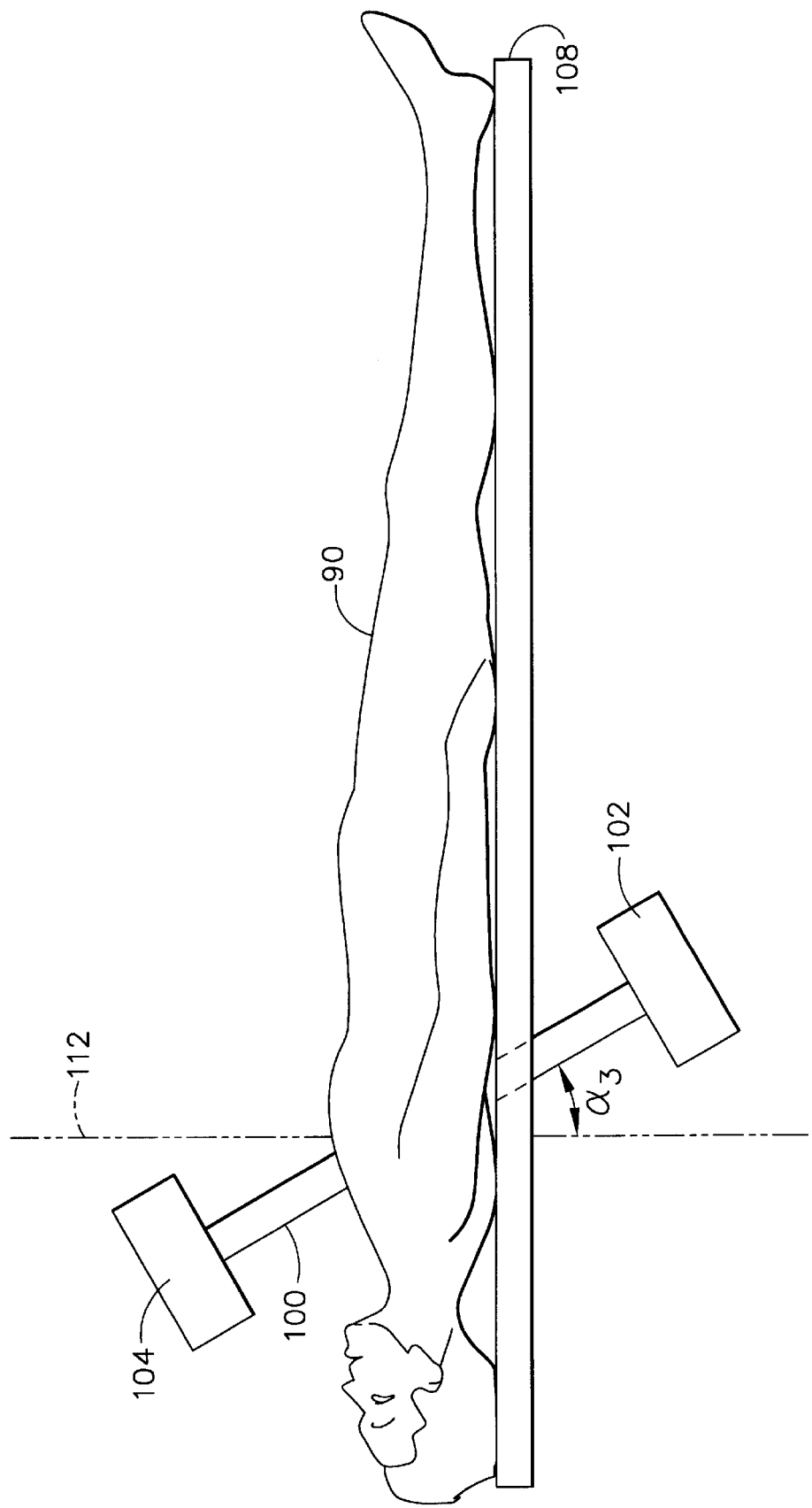
FIG. 9C and FIG. 9D are schematic views of a C-arm taking fluoroscopic images of a chamber of a heart of a patient from the cranial and caudal projections, respectively.
Figure 9D:
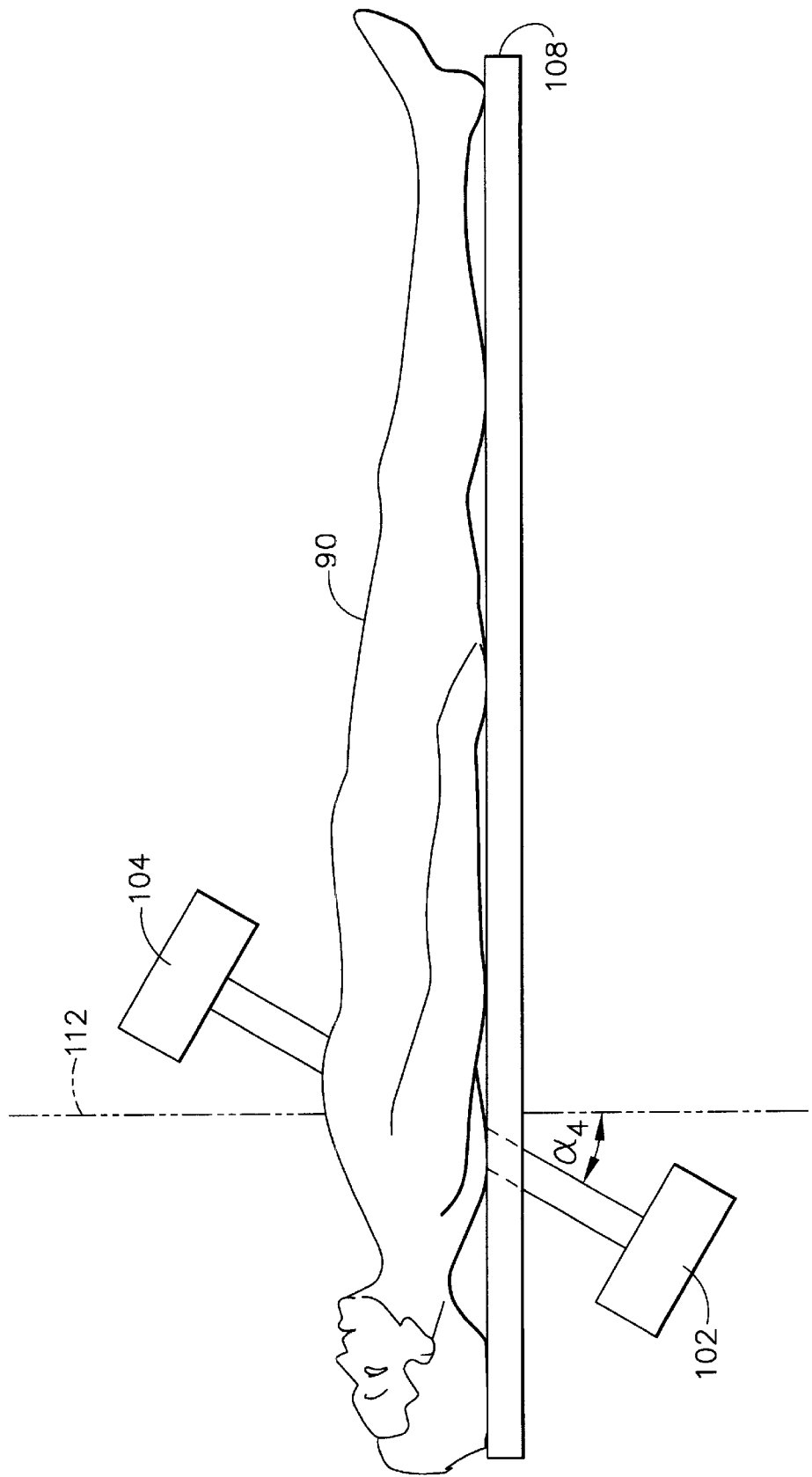

The C-arm 100 may also be inclined with the image intensifier 104 facing the patient's head (cranial projection) or facing the patient's feet (caudal projection). FIGS. 9C and 9D show the C-arm inclined in the cranial and caudal direction perspective, respectively. Preferably, the projection angle of the images in the cranial-caudal perspective ($\alpha_3$ in the cranial perspective and $\alpha_4$ in the caudal perspective) is less than about 10 degrees. More preferably, the cranial-caudal projection angle of the images is about zero degrees.

The projection angles of each of the images in the left-right perspective and in the caudal-cranial perspective are noted for later use in the method of the invention. Also, the two-dimensional location of the registration position sensor in the chamber images is noted for later use in the method of the invention. The registration sensor location in the images may be annotated manually or automatically as hereinbefore described.

Figure 9E:
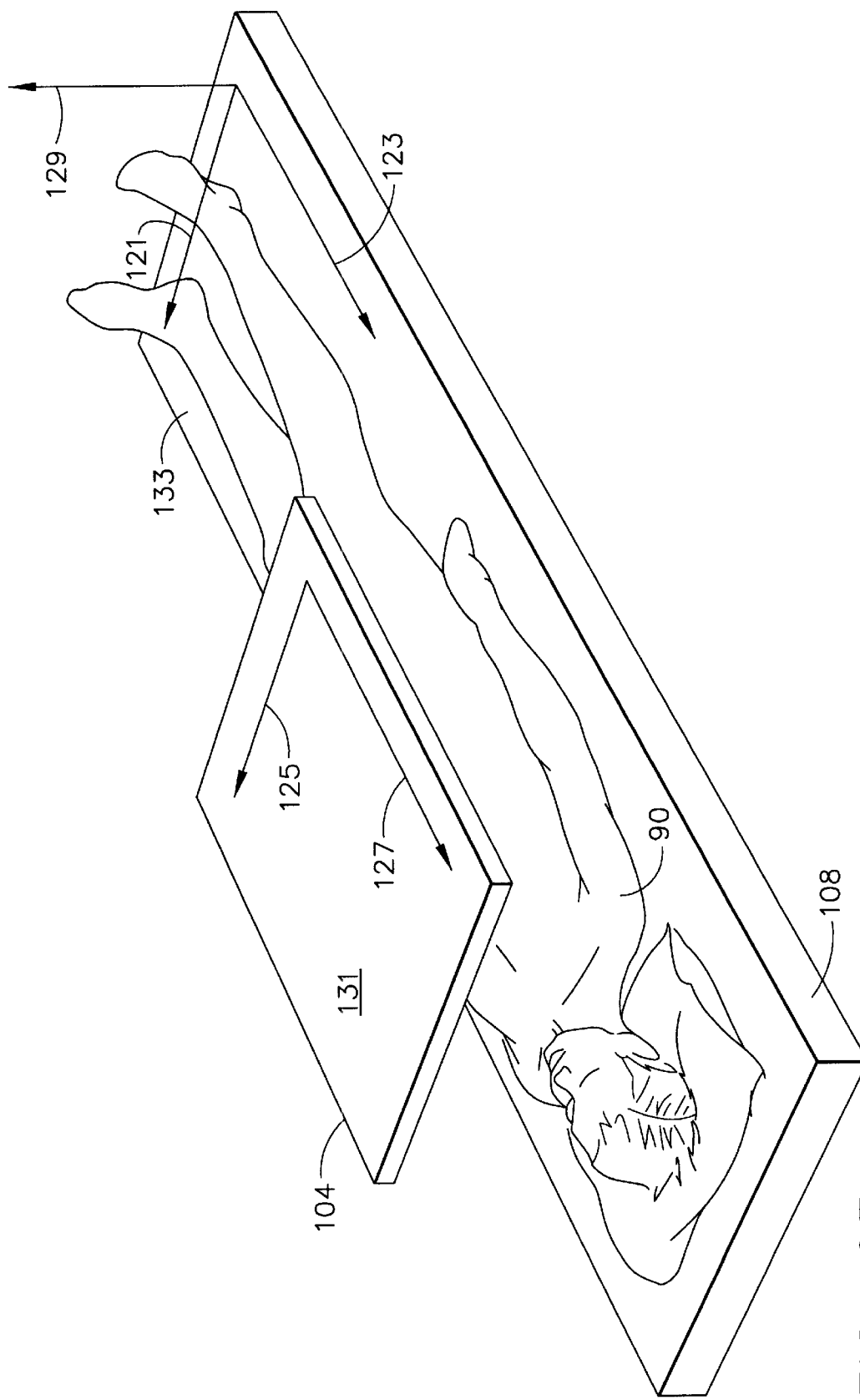
FIG. 9E is a schematic view of a patient showing the coordinate systems of a position sensor location system and a fluoroscopy imaging system.

FIG. 9E shows the coordinate systems of both the position sensor location system and the fluoroscopy imaging system. The X axis 121 and the Y axis 123 of the position sensor location system are parallel to the respective X axis 125 and the Y axis 127 of the image intensifier 104 of the fluoroscopy system when the C-arm 100 is not inclined, i.e., when the C-arm 100 is at an angle of zero degrees with respect to both the right-left and the cranial-caudal perspectives. As shown in FIG. 9E, the Y axes (123 and 127) run from the caudal end (foot) to the cranial end (head) of the patient and the X axes (121 and 125) runs from the patient's right to left, perpendicular to the Y axis. The Z axis 129 of the position sensor location system runs orthogonal to the system's X and Y axes (121 and 123 respectively). The X-Y plane 131 of the fluoroscopy image is parallel to the X-Y plane 133 of the position sensor location system. Thus, the projection angle of the fluoroscopy images with respect to the image intensifier 104 in the uninclined position will be equal to the projection angle of the images with respect to the position sensor location system.

Knowing the projection angles of each of the images relative to the position sensor location system frame of reference, the two dimensional coordinates of the registration position sensor 124 in the images, the three-dimensional coordinates of the registration position sensor 124 in the position sensor location system frame of reference and the image scaling factors (as described below), the three-dimensional coordinates of each point in the images may be computed using standard linear algebra techniques.

Once the chamber images are acquired and the end diastole frames are selected, topological information, preferably in the form of the chamber contour, is identified and marked in the images as hereinabove described.

Figure 10A:
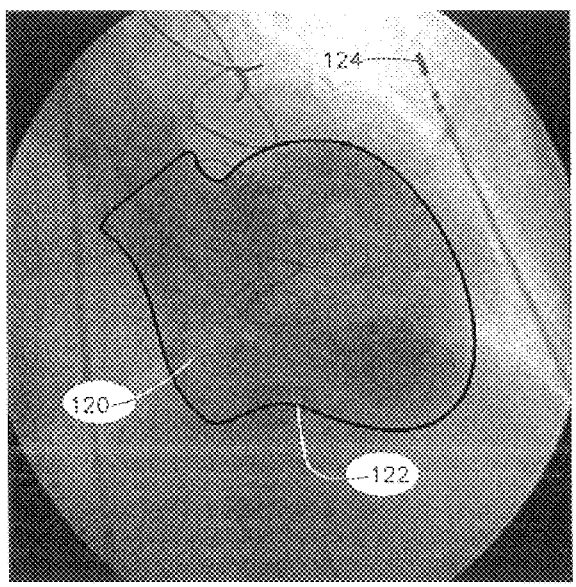
FIG. 10A and FIG. 10B are contrast-assisted fluorograms of the left ventricle of a patient taken from the RAO and LAO projections, respectively.
Figure 10B:
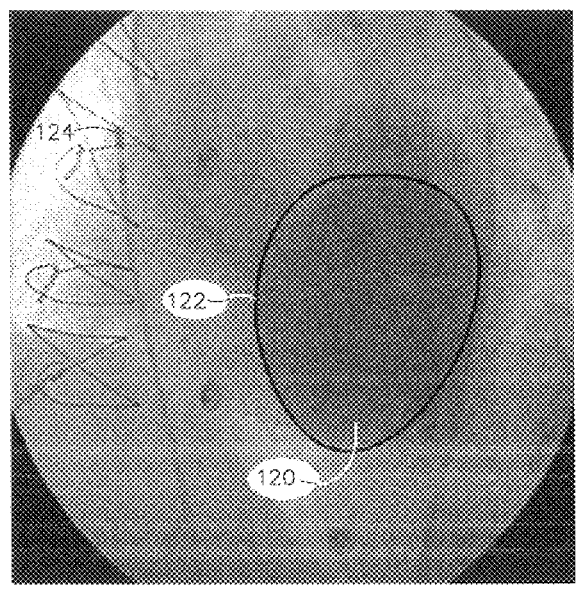

FIGS. 10A and 10B show RAO and LAO contrast-assisted fluorograms of a left ventricle 120. Included in these figures is the delineated contour 122 of the ventricle 120 as well as an image of registration sensor 124 that is contained in a catheter adhered or taped to the chest of a patient.

The scaled chamber images containing the extracted chamber contours are then merged with respect to the position sensor location system to meet the following conditions:

(1) The registration position sensor 124 in the images is located at its measured three-dimensional coordinates; and (2) The images are oriented with respect to each other according to the relative orientation of the projections from which the images were taken.

Figure 11:
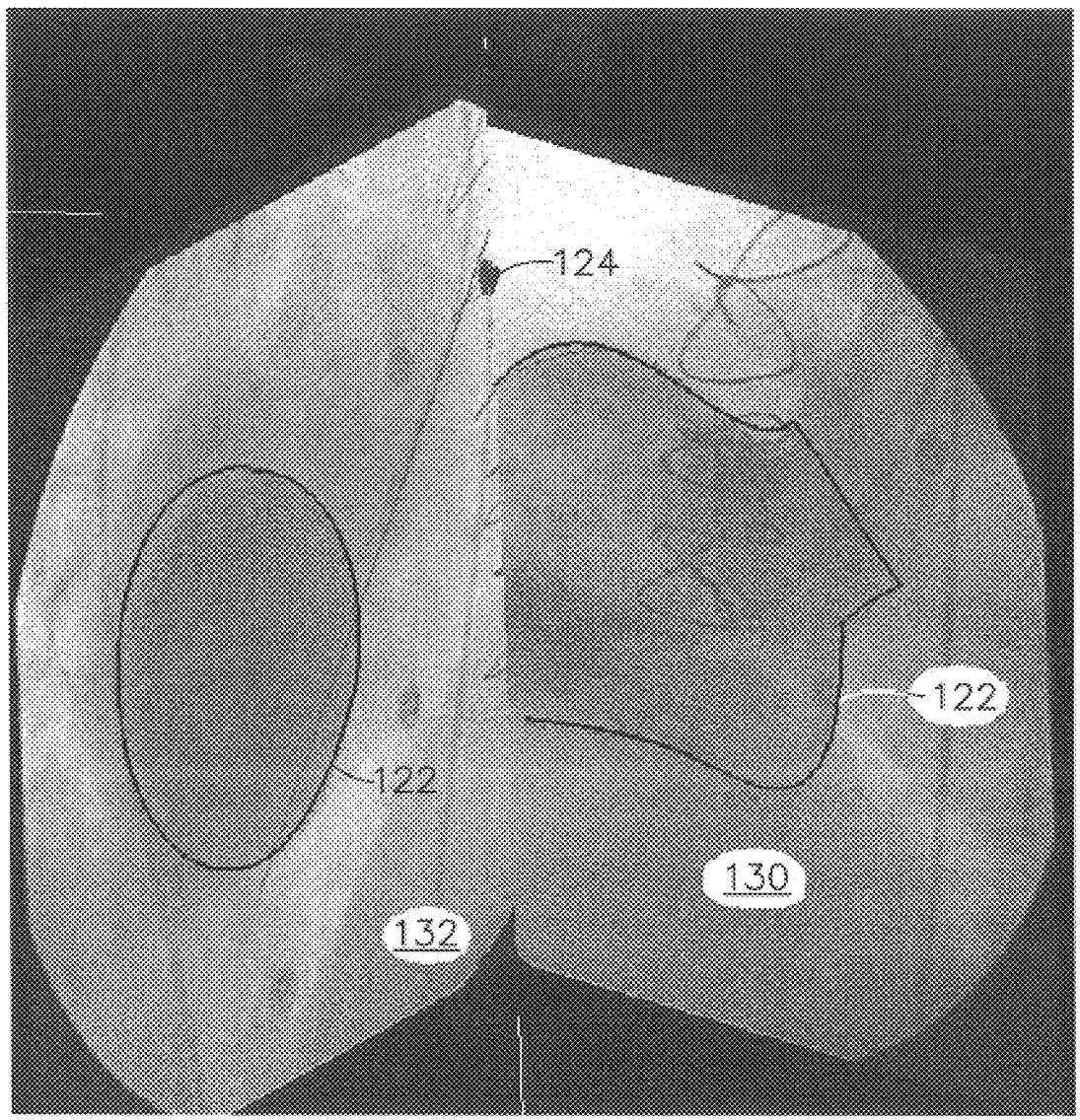
FIG. 11 shows the fluorograms of FIG. 10A and FIG. 10B in registration with a position sensor location system frame of reference.

FIG. 11 shows the two merged images, 130 and 132 of the ventricle of FIGS. 10A and 10B taken from the RAO and the LAO projections, respectively. The chamber contour 122 has been identified in each of the images. The images are registered such that location of registration position sensor 124 in the images coincides with its measured location in the position sensor frame of reference. The images are oriented with respect to each other corresponding to the relative orientation of the projections from which the images were taken.

Figure 12:
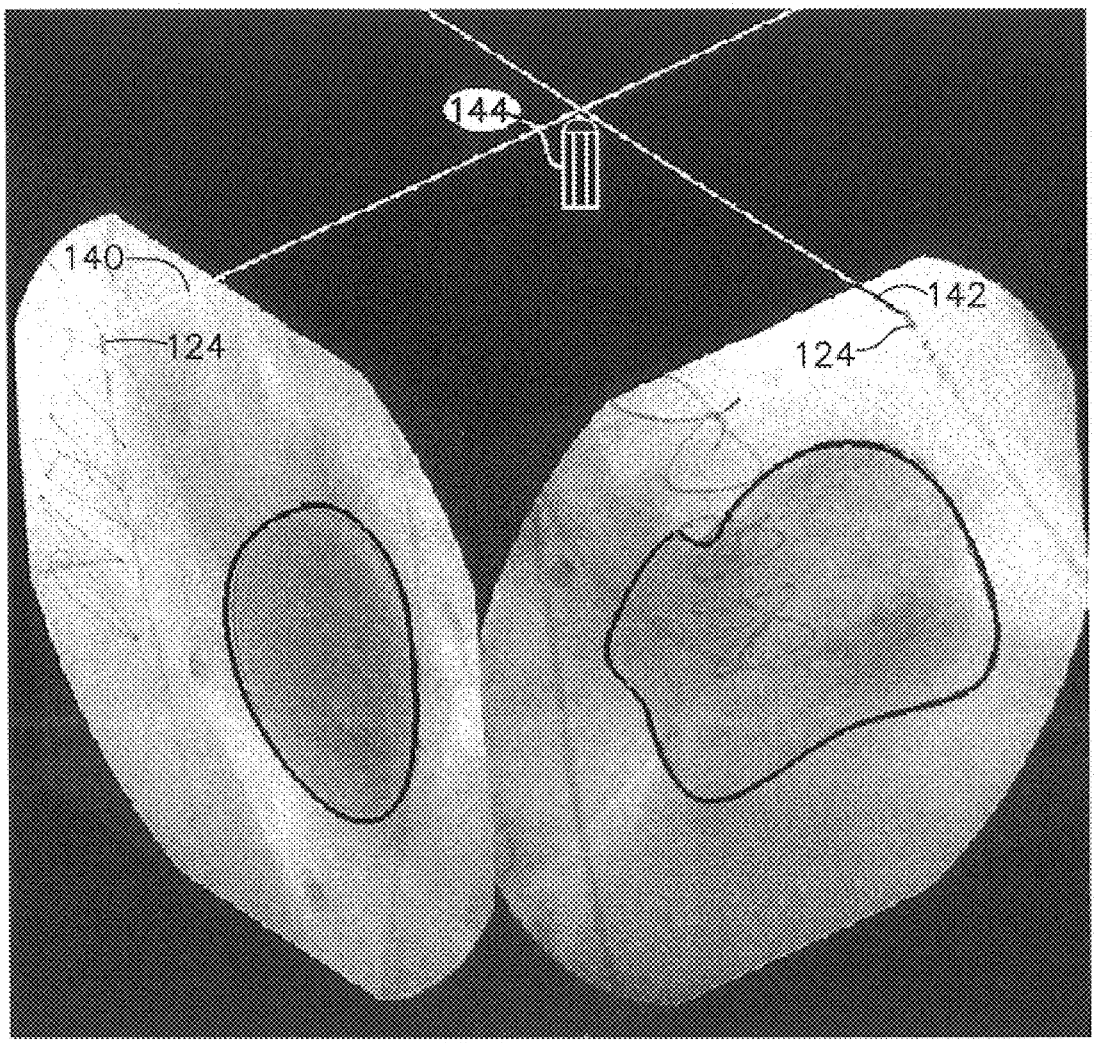
FIG. 12 shows the fluorograms of FIG. 11 separated from each other along directions normal to the respective images.

Topological information contained in or derived from the chamber images is used to guide the navigation of the mapping catheter 21 to individual points in the chamber for purposes of acquiring condition and position information at each of the points. The acquisition points are preferably on the wall of the chamber. The topological information used to guide the navigation is preferably a reconstruction, more preferably, a three-dimensional reconstruction of the chamber based on topological information contained in or derived from the chamber images. A three dimensional reconstruction of the chamber is performed as follows:

To aid in visualizing the reconstruction process, the merged images may be moved apart along vectors (lines) normal to each image emanating from the coordinates of the registration position sensor. FIG. 12 shows the two chamber images of FIG. 11 that have been separated in this fashion. The images are separated along vectors 140, 142 emanating from the registration position sensor 124 in each of the images. A graphic 144 representing the registration position sensor at its correct location in the position sensor location system frame of reference is shown in FIG. 12 at the intersection of these lines.

The algorithm for the three dimensional reconstruction of the chamber from the contours of the individual chamber images is illustrated schematically in FIGS. 13A–13F, each of which contains two ovals representing the contours of the chamber in the RAO and LAO projections. In the following process description, we refer to lines emanating from the contours. All of these lines are normal to the respective chamber images from which they emanate. Points on the reconstruction are formed, in principle, by the intersection of lines emanating from the RAO and LAO projections. In practice, these lines will not always intersect due to errors associated with the system such as measurement errors and patient movement. Accordingly, a threshold distance is defined such that lines separated by less than the threshold distance are considered to have intersected for purposes of the reconstruction algorithm.

The magnitude of the threshold distance will depend on the distance between points on the contour that are sampled by the algorithm. The larger the distance between points on the contour, the greater will be the distance separating the lines passing through these points. While a small distance between points gives a more accurate reconstruction, a small distance between points means processing a greater number of points, which is more computationally intensive. Empirically, it was found that a distance between points of about 1.0 mm and a threshold of about 1.0 mm strike a reasonable balance between reconstruction accuracy and computational intensity.

Step 1. Begin by producing a line (line A in FIG. 13A) passing through a point on the RAO contour.

Figure 13A:
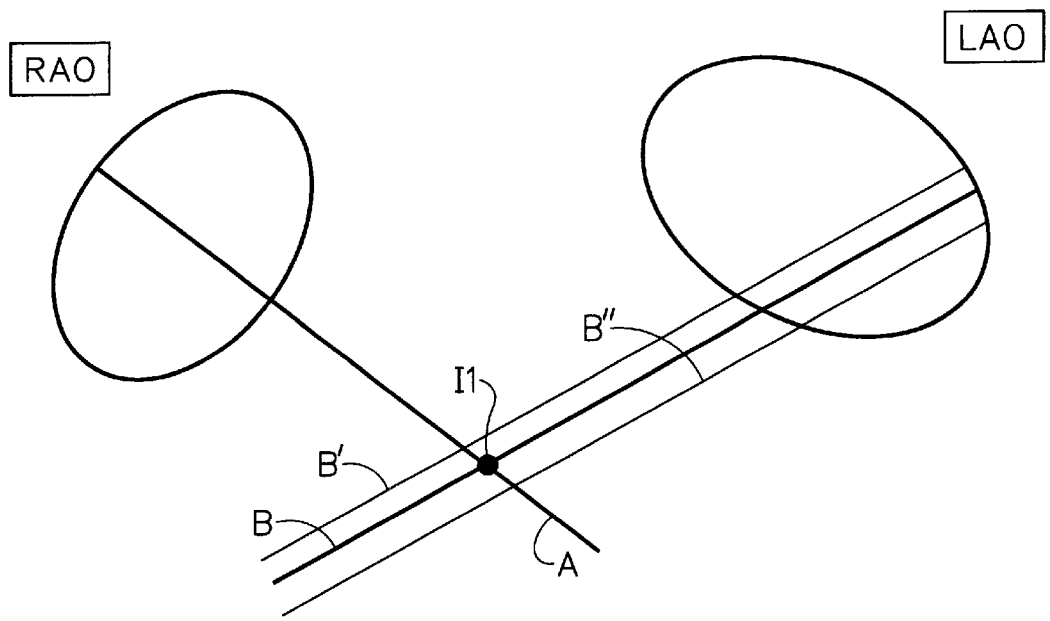
FIG. 13A–FIG. 13F schematically depict the steps of an algorithm to reconstruct a chamber of a heart from contour information contained in two chamber images.

Step 2. Next, find the line emanating from the LAO contour that is closest to line A. FIG. 13A shows three lines emanating from the LAO contour, labeled B, B' and B". The closest LAO contour line to line A is defined as the LAO contour line that has the shortest mathematical distance to line A. The line emanating from the LAO contour that is closest to line A is shown as line B in FIG. 13A. The projection of line B on line A is the point on line A that is closest to line B. This point is shown as point I1 in FIG. 13A.

Figure 13B:
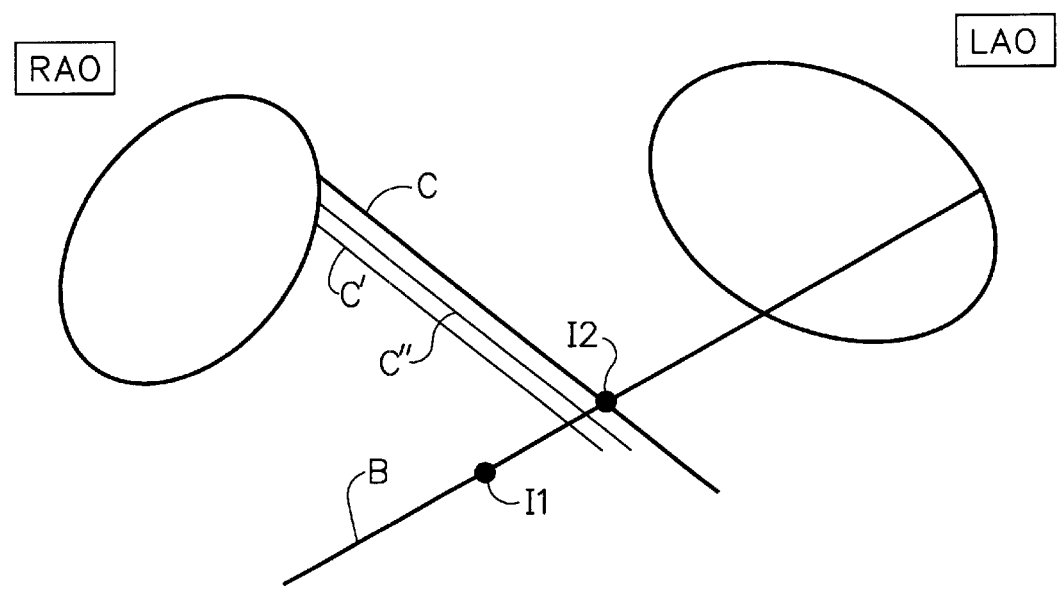

Step 3. Next, consider all lines emanating from the RAO contour that are closer to line B then the predefined threshold distance. In other words, find all RAO lines that have a mathematical distance to line B below the predefined threshold distance. In FIG. 13B, lines C, C' and C" are all below the predefined threshold distance. Of these RAO lines, choose a line C whose projection on line B is furthest from point I1 The projection of line C on line B is shown in FIG. 13B as the point 12.

Figure 13C:
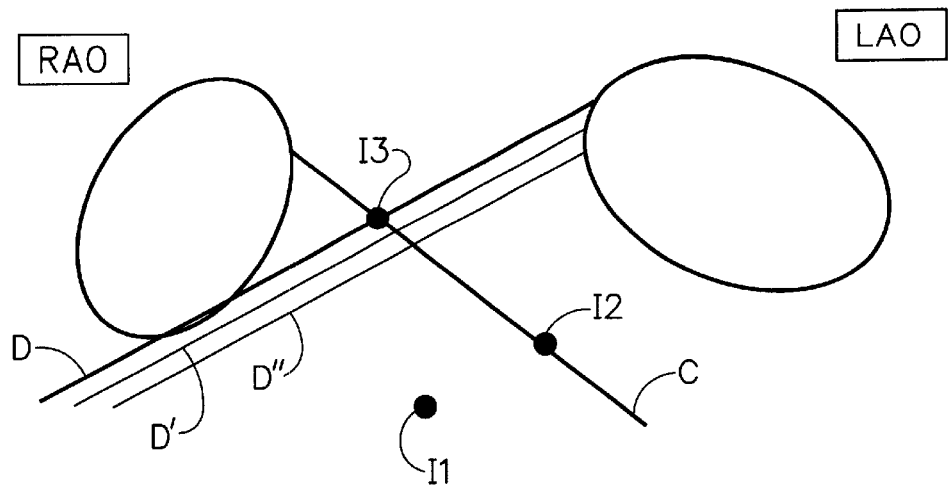

Step 4. Next, consider lines emanating from the LAO contour (lines D, D' and D" in FIG. 13C) that are closer to line C then the predefined threshold distance. Of these, choose a line D whose projection on line C is furthest from point 12. The projection of line D on line C is shown in FIG. 13C as the point 13.

Figure 13D:
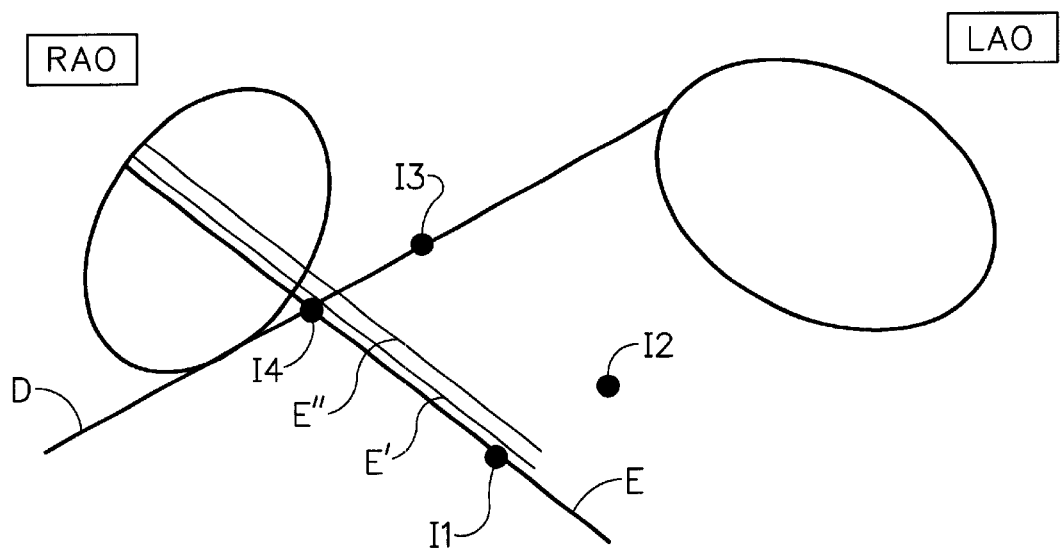

Step 5. Now, consider lines emanating from the RAO contour (lines E, E' and E" in FIG. 13D) that are closer to line D then the predefined threshold. Of these, choose line E whose projection on line D is furthest from point 13. The projection of line E on line D is shown in FIG. 13D as point 14.

Figure 13E:
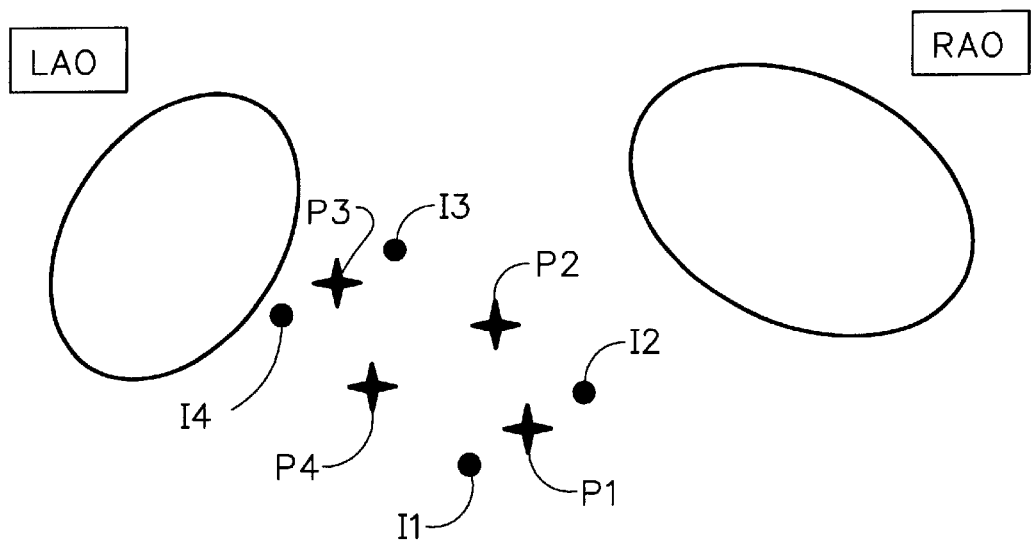
Figure 13F:
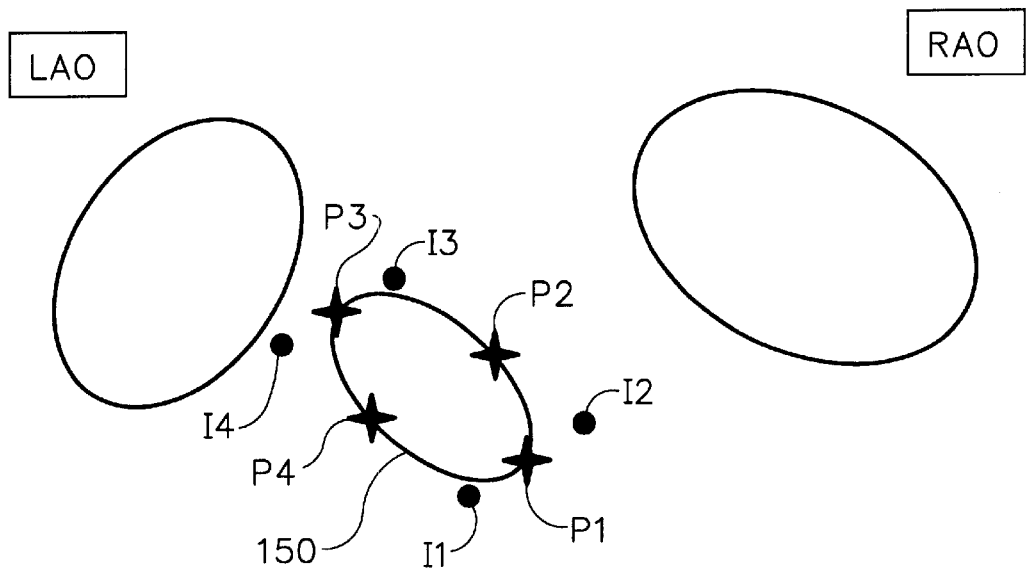

Step 6. Calculate a curve that is circumscribed by the points I1, I2, I3 and I4 as follows: Define point P1 as the center of the segment between points I1 and I2; point P2 as the center of the segment between points I2 and I3; point P3 as the center of the segment between points I3 and I4; and point P4 as the center of the segment between points I4 and I1 (FIG. 13E). Then, calculate the interpolation spline that passes through the points P1, P2, P3, P4, i.e., the curve 150 in FIG. 13F. Calculate the spline through the midpoints between the line intersections to produce a more smoothly shaped reconstruction that is ellipsoidal in cross-section and is a more accurate representation of the chamber. The points on the spline are saved as new points for the three-dimensional reconstruction of the chamber.

Step 7. Each of above steps of the reconstruction is repeated for all lines passing through the RAO contour.

Step 8. Once all of the RAO contour lines are processed, the above steps are repeated for all lines emanating from the LAO contour.

Figure 14:
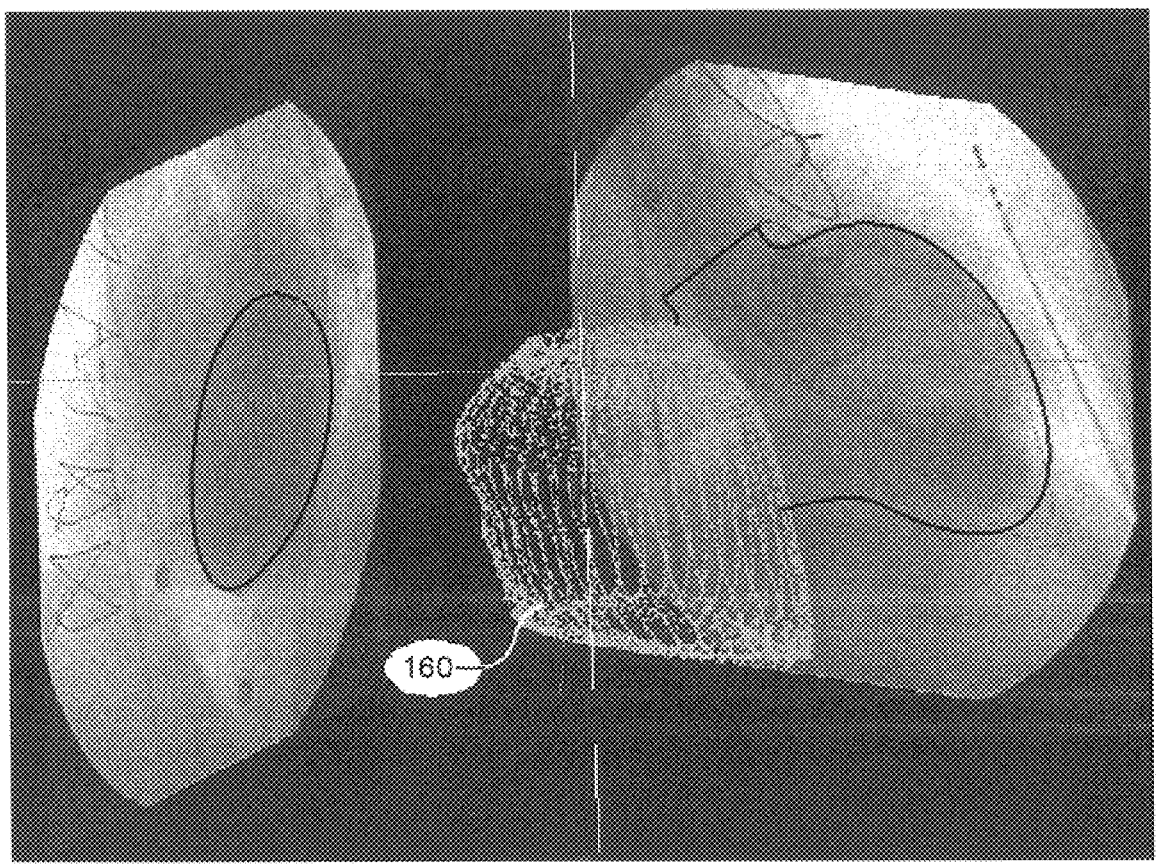
FIG. 14 shows the reconstruction of the heart chamber using the algorithm depicted in FIG. 13A–FIG. 13F.

The reconstruction 160, from points produced by this algorithm, is shown in FIG. 14. As shown in FIG. 14, the algorithm provides a reconstruction with a smooth shape that can be used to guide the navigation of a catheter to points within the chamber for the purpose of acquiring condition and location information at said points.

The reconstruction of the cardiac chamber as described above was accomplished from two chamber images. Similar techniques may be employed for reconstructions from more than two images. Alternatively, back projection techniques, as described in "Fundamentals of Digital Image Processing" by Anil K. Jain, Prentice Hall, Englewood Cliffs, N.J. 1989, pp. 439–445, may be used in reconstructing the cardiac chamber from a plurality of chamber images.

Having derived reconstruction 160 of chamber 120 shown in FIG. 14 in the frame of reference of the position sensor location system, the reconstruction is used to guide the navigation of the mapping catheter distal tip to points in the chamber at which condition information is desired to be acquired, preferably adjacent to or in contact with the chamber wall. Condition information is acquired via at least one sensor contained at the catheter distal tip at each of said points. Condition information is acquired at a sufficient number of points throughout the chamber to permit the generation of a map of the condition in the chamber.

The display of the reconstruction preferably contains a graphic to indicate the location of the mapping catheter tip in real time during navigation of the catheter tip and acquisition of condition and position information. As with the previously described embodiment, the display may be marked at the points of data acquisition to indicate to the operator the chamber locations where condition information has been sampled and to guide the operator to additional sampling points in order to obtain a map that is completely representative of the chamber. In addition, the display may be annotated to indicate values of the condition information either during or after information acquisition. The display may be annotated with numerical values of the condition information at each one of the acquisition points. Alternatively, the map may be color coded so that the colors are indicative of the value of the condition at each point in the map. Condition information between acquisition points may be interpolated from the values at the acquisition points, with the interpolated values likewise displayed according to either of the above-mentioned methods.

A major advantage of the method and apparatus of the invention is that once the images of the chamber are acquired and the topological features of the chamber have been ascertained, the catheter tip may be navigated to points within the heart for the acquisition of condition information entirely under the guidance of the topological information contained in or derived from the images without any additional imaging during the acquisition of condition information. Consequently, condition information may be acquired without using fluoroscopy during the acquisition step, resulting in significant reductions in radiation exposure to the patient undergoing the procedure.

Although, the invention has been described in the context of mapping the left ventricle of the heart, the method may be used in mapping any of the heart's chambers. Furthermore, the chamber reconstruction as described herein may be decoupled from the chamber mapping. For example, the reconstruction of the left ventricle may be used to provide an anatomical reference for mapping other portions of the heart such as the right atrium.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A method for intracardially mapping a condition of a chamber of a heart of a subject, said method comprising the steps of:

a) providing a catheter having a distal tip, said catheter distal tip having at least one sensor contained therein or proximate thereto, said at least one sensor being capable of sensing condition information of said chamber and providing three-dimensional position information of the catheter tip in a positional frame of reference;

b) acquiring a first image of said chamber, said first image taken from a first projection and containing topological information of said chamber;

c) acquiring a second image of said chamber, said second image taken from a second projection different from said first projection, said second image containing topological information of said chamber, and wherein said first projection and said second projection are separated by an angle of about 75 degrees to about 105 degrees.

d) registering said first image and said second image with said positional frame of reference;

e) advancing said distal tip of said catheter into said chamber;

f) navigating said distal tip of said catheter proximate an acquisition point in said chamber, said navigation guided by topological information contained in or derived from said first and said second images;

g) acquiring condition information and position information at said acquisition point with said at least one sensor;

h) repeating step (f) and (g) at additional acquisition points to generate a map of said condition in said chamber.

2. A method of mapping a chamber of a heart according to claim 1 wherein said condition is an electrical condition.

3. A method of mapping a chamber of a heart according to claim 1 wherein said condition is a mechanical condition.

4. A method of mapping a chamber of a heart according to claim 1 wherein said condition is an electromechanical condition.

5. A method of mapping a chamber of a heart according to claim 1 wherein said chamber is a left ventricle.

6. A method of mapping a chamber of a heart according to claim 1 wherein said at least one sensor comprises a position sensor capable of providing said three-dimensional position information, said position sensor further providing mechanical condition information.

7. A method of mapping a chamber of a heart according to claim 1 wherein said at least one sensor comprises a position sensor capable of providing said three-dimensional position information and an electrode for sensing electrical information.

8. A method of mapping a chamber of a heart according to claim 1 wherein said at least one sensor comprises an electromagnetic sensor, said electromagnetic sensor generating signals responsive to the strength of a magnetic field external to the patient, said signals indicative of the three-dimensional position of the sensor in said frame of reference.

9. A method of mapping a chamber of a heart according to claim 1 wherein said first and said second images of said chamber are contrast-assisted fluoroscopic images.

10. A method of mapping a chamber of a heart according to claim 1 wherein each of said first and said second images depict the chamber at the same phase of the cardiac cycle.

11. A method of mapping a chamber of a heart according to claim 10 wherein each of said first and said second images depict the chamber in end-diastole.

12. A method of mapping a chamber of a heart according to claim 1 wherein said topological information comprises the chamber contour.

13. A method of mapping a chamber of a heart according to claim 1 which further comprises acquiring an image of a scaling object from each of said first and said second projections.

14. A method of mapping a chamber of a heart according to claim 13 wherein said images of said scaling object are used to scale said images of said chamber.

15. A method of mapping a chamber of a heart according to claim 1 which further comprises affixing a registration position sensor to said patient prior to acquisition of said first and said second images of said chamber, wherein said chamber images include an image of said registration position sensor.

16. A method of mapping a chamber of a heart according to claim 15 which further comprises determining the three-dimension al position coordinates of said registration position sensor, and using said determined position coordinates to register said images of said chamber in said frame of reference.

17. A method of mapping a chamber of a heart according to claim 1 wherein said topological information used to guide said catheter tip to said acquisition points comprises a reconstruction of said chamber.

18. A method of mapping a chamber of a heart according to claim 17 wherein said reconstruction is a three-dimensional reconstruction.

19. A method of mapping a chamber of a heart according to claim 1 which further comprises the step of creating a map of said chamber from said acquired condition and position information.

20. A method for intracardially mapping a condition of a chamber of a heart of a subject, said method comprising the steps of:

a) providing a mapping catheter having a distal tip, said catheter distal tip having at least one sensor contained therein or proximate thereto, said at least one sensor being capable of sensing condition information of said chamber and providing three-dimensional position information of the catheter tip in a positional frame of reference;

b) providing a reconstruction of topological features of said chamber registered with said positional frame of reference, and wherein said reconstruction is based on;
   i) a first image of said chamber taken from a first projection, and
   ii) a second image of said chamber taken from a second projection, wherein each of said first and said second images contain topological information of said chamber, and wherein said first projection and said second projection are separated by an angle of about 75 degrees to about 105 degrees;

c) advancing said distal tip of said catheter into said chamber;

d) navigating said distal tip of said catheter proximate an acquisition point in said chamber, said navigation guided by said topological features of said reconstruction;

e) acquiring condition information and position information at said acquisition point with said at least one sensor;

f) repeating step (d) and (e) at additional acquisition points throughout the chamber to generate a map of said condition in said chamber.

21. A method of mapping a chamber of a heart according to claim 20 wherein said reconstruction is a three dimensional reconstruction.

22. A method of mapping a chamber of a heart according to claim 20 wherein said first and said second images of said chamber are contrast-assisted fluoroscopic images.

23. A method of mapping a chamber of a heart according to claim 20 wherein each of said first and said second images depict the chamber at the same phase of the cardiac cycle.

24. A method of mapping a chamber of a heart according to claim 20 wherein each of said first and said second images depict the chamber in end-diastole.

25. A method of mapping a chamber of a heart according to claim 20 wherein said topological information comprises the chamber contour.

26. A method of mapping a chamber of a heart according to claim 20 which further comprises acquiring an image of a scaling object from each of said first and said second projections.

27. A method of mapping a chamber of a heart according to claim 26 wherein said images of said scaling object are used to scale said images of said chamber.

28. A method of mapping a chamber of a heart according to claim 20 which further comprises affixing a registration position sensor to said patient prior to acquisition of said first and said second images of said chamber, wherein said chamber images include an image of said registration position sensor.

29. A method of mapping a chamber of a heart according to claim 28 which further comprises determining the three-dimensional position coordinates of said registration position sensor, and using said determined position coordinates to register said images of said chamber in said frame of reference.

30. A method of mapping a chamber of a heart according to claim 20 wherein said condition is an electrical condition.

31. A method of mapping a chamber of a heart according to claim 20 wherein said condition is a mechanical condition.

32. A method of mapping a chamber of a heart according to claim 20 wherein said condition is an electromechanical condition.

33. A method of mapping a chamber of a heart according to claim 20 wherein said chamber is a left ventricle.

34. A method of mapping a chamber of a heart according to claim 20 wherein said at least one sensor comprises a position sensor capable of providing said three-dimensional position information, said position sensor further providing mechanical condition information.

35. A method of mapping a chamber of a heart according to claim 20 wherein said at least one sensor comprises a position sensor capable of providing said three-dimensional position information and an electrode for sensing electrical information.

36. A method of mapping a chamber of a heart according to claim 20 wherein said at least one sensor comprises an electromagnetic sensor, said electromagnetic sensor generating signals responsive to the strength of a magnetic field external to the patient, said signals indicative of the three-dimensional position of the sensor in said frame of reference.

37. A method of mapping a chamber of a heart according to claim 20 which further comprises the step of creating a map of said chamber from said acquired condition and position information.

38. Apparatus for intracardially mapping a condition of a chamber of a heart of a subject comprising:
   a) a catheter having a distal tip, said catheter distal tip having at least one sensor contained therein or proximate thereto, said at least one sensor being capable of sensing condition information of said chamber and providing three-dimensional position information of the catheter tip in a frame of reference;
   b) image processing circuitry for registering a first image of said chamber and a second image of said chamber with said positional frame of reference, said first image and said second image taken from a first projection and a second projection relative to said chamber, said images containing topological information of said chamber, and wherein said first projection and said second projection are separated by an angle of about 75 degrees to about 105 degrees;
   c) signal processing circuits for acquiring condition information and position information at a plurality of acquisition points in said chamber with said at least one sensor, said condition and position information permitting the generation of a map of said condition in said chamber.

39. Apparatus for mapping a chamber of a heart according to claim 38 wherein said at least one sensor comprises a position sensor capable of providing said three-dimensional position information and an electrode for sensing electrical information.

40. Apparatus for mapping a chamber of a heart according to claim 38 wherein said at least one sensor comprises an electromagnetic sensor, said electromagnetic sensor generating signals responsive to the strength of a magnetic field external to the patient, said signals indicative of the three-dimensional position of the sensor in said frame of reference.

41. Apparatus for mapping a chamber of a heart according to claim 38 which further comprises a scaling object.

42. Apparatus for mapping a chamber of a heart according to claim 38 which further comprises a registration position sensor to register said images with said frame of reference.

43. Apparatus for mapping a chamber of a heart according to claim 38 which further comprises image processing circuits for constructing a reconstruction of said chamber from said topological information contained in said images.

44. Apparatus for mapping a chamber of a heart according to claim 38 wherein said reconstruction is a three-dimensional reconstruction.

45. Apparatus for mapping a chamber of a heart according to claim 38 which further comprises circuits for mapping said condition of said chamber using said condition information and said position information.

46. Apparatus for intracardially mapping a condition of a chamber of a heart of a subject comprising:
   a) a catheter having a distal tip, said catheter distal tip having at least one sensor contained therein or proximate thereto, said at least one sensor being capable of sensing condition information of said chamber and providing three-dimensional position information of the catheter tip in a frame of reference;
   b) image processing circuits for constructing a topological reconstruction of said chamber registered with said frame of reference, said topological reconstruction including a first image of said chamber, said first image taken from a first projection and a second image of said chamber, said second image taken from a second projection different from said first projection, and wherein said first image and said second image are taken from an LAO projection and an RAO projection;
   c) signal processing circuits for acquiring condition information and position information at a plurality of acquisition points in said chamber with said at least one sensor, said condition information and position information permitting the generation of a map of said condition in said chamber.

47. Apparatus for mapping a condition of a chamber of a heart of claim 46 wherein said reconstruction is a three dimensional reconstruction.

48. Apparatus for mapping a chamber of a heart according to claim 46 wherein said at least one sensor comprises a position sensor capable of providing said three-dimensional position information and an electrode for sensing electrical information.

49. Apparatus for mapping a chamber of a heart according to claim 46 wherein said at least one sensor comprises an electromagnetic sensor, said electromagnetic sensor generating signals responsive to the strength of a magnetic field external to the patient, said signals indicative of the three-dimensional position of the sensor in said frame of reference.

50. Apparatus for mapping a chamber of a heart according to claim 46 which further comprises a scaling object.

51. Apparatus for mapping a chamber of a heart according to claim 46 which further comprises a registration position sensor to register said images with said frame of reference.

52. A method for intracardially mapping a condition of a chamber of a heart of a subject, said method comprising the steps of:
   a) providing a catheter having a distal tip, said catheter distal tip having at least one sensor contained therein or proximate thereto, said at least one sensor being capable of sensing condition information of said chamber and providing three-dimensional position information of the catheter tip in a positional frame of reference;
   b) acquiring a first image of said chamber, said first image taken from a first projection and containing topological information of said chamber;
   c) acquiring a second image of said chamber, said second image taken from a second projection different from said first projection, said second image containing topological information of said chamber, and wherein said first image and said second image are taken from an LAO projection and an RAO projection;
   d) registering said first image and said second image with said positional frame of reference;
   e) advancing said distal tip of said catheter into said chamber;
   f) navigating said distal tip of said catheter proximate an acquisition point in said chamber, said navigation guided by topological information contained in or derived from said first and second images;
   g) acquiring condition information and position information at said acquisition point with said at least one sensor;
   h) repeating step (f) and (g) at additional acquisition points to generate a map of said condition in said chamber.

53. A method of mapping a chamber of a heart according to claim 52 wherein said condition is an electrical condition.

54. A method of mapping a chamber of a heart according to claim 52 wherein said condition is a mechanical condition.

55. A method of mapping a chamber of a heart according to claim 52 wherein said condition is an electromechanical condition.

56. A method of mapping a chamber of a heart according to claim 52 wherein said chamber is a left ventricle.

57. A method of mapping a chamber of a heart according to claim 52 wherein said at least one sensor comprises a position sensor capable of providing said three-dimensional position information, said position sensor further providing mechanical condition information.

58. A method of mapping a chamber of a heart according to claim 52 wherein said at least one sensor comprises a position sensor capable of providing said three-dimensional position information and an electrode for sensing electrical information.

59. A method of mapping a chamber of a heart according to claim 52 wherein said at least one sensor comprises an electromagnetic sensor, said electromagnetic sensor generating signals responsive to the strength of a magnetic field external to the patient, said signals indicative of the three-dimensional position of the sensor in said frame of reference.

60. A method of mapping a chamber of a heart according to claim 52 wherein said first and said second images of said chamber are contrast-assisted fluoroscopic images.

61. A method of mapping a chamber of a heart according to claim 52 wherein each of said first and second images depict the chamber at the same phase of the cardiac cycle.

62. A method of mapping a chamber of a heart according to claim 61 wherein each of said first and said second images depict the chamber in end-diastole.

63. A method of mapping a chamber of a heart according to claim 52 wherein said topological information comprises the chamber contour.

64. A method of mapping a chamber of a heart according to claim 52 which further comprises acquiring an image of a scaling object from each said first and said second projections.

65. A method of mapping a chamber of a heart according to claim 64 wherein said images of said scaling object are used to scale said images of said chamber.

66. A method of mapping a chamber of a heart according to claim 52 which further comprises affixing a registration position sensor to said patient prior to acquisition of said first and said second images of said chamber, wherein said chamber images include an image of said registration position sensor.

67. A method of mapping a chamber of a heart according to claim 66 which further comprises determining the three-dimensional position coordinates of said registration position sensor, and using said determined position coordinates to register said images of said chamber in said frame of reference.

68. A method of mapping a chamber of a heart according to claim 52 wherein said topological information used to guide said catheter tip to said acquisition points comprises a reconstruction of said chamber.

69. A method of mapping a chamber of a heart according to claim 68 wherein said reconstruction is a three-dimensional reconstruction.

70. A method of mapping a chamber of a heart according to claim 46 which further comprises the step of creating a map of said acquired condition and position information.

71. A method for intracardially mapping a condition of a chamber of a heart of a subject, said method comprising the steps of:
   a) providing a mapping catheter having a distal tip, said catheter distal tip having at least one sensor contained therein or proximate thereto, said at least one sensor being capable of sensing condition information of said chamber and providing three-dimensional position information of the catheter tip in a positional frame of reference;
   b) providing a reconstruction of topological features of said chamber registered with said positional frame of reference, and wherein said reconstruction is based on:
      i) a first image of said chamber taken from a first projection, and
      ii) a second image of said chamber taken from a second projection, wherein each of said first and said second images contain topological information of said chamber, and wherein said first image and said second image are taken from an LAO projection and an RAO projection;
   c) advancing said distal tip of said catheter into said chamber;
   d) navigating said distal tip of said catheter proximate an acquisition point in said chamber, said navigation guided by said topological features of said reconstruction;
   e) acquiring condition information and position information at said acquisition point with said at least one sensor;
   f) repeating step (d) and (e) at additional acquisition points throughout the chamber to generate a map of said chamber.

72. A method of mapping a chamber of a heart according to claim 71 wherein said reconstruction is a three-dimensional reconstruction.

73. A method of mapping a chamber of a heart according to claim 71 wherein said first and said second images of said chamber are contrast-assisted fluoroscopic images.

74. A method of mapping a chamber of a heart according to claim 71 wherein each of said first and said second images depict the chamber at the same phase of the cardiac cycle.

75. A method of mapping a chamber of a heart according to claim 71 wherein each of said first and said second images depict the chamber in end-diastole.

76. A method of mapping a chamber of a heart according to claim 71 wherein said topological information comprises the chamber contour.

77. A method of mapping a chamber of a heart according to claim 71 which further comprises acquiring an image of a scaling object from each of said first and said second projections.

78. A method of mapping a chamber of a heart according to claim 77 wherein said images of said scaling object are used to scale said images of said chamber.

79. A method of mapping a chamber of a heart according to claim 71 which further comprises affixing a registration position sensor to said patient prior to acquisition of said first and said second images of said chamber, wherein said chamber images include an image of said registration position sensor.

80. A method of mapping a chamber of a heart according to claim 79 which further comprises determining the three-dimensional position coordinates of said registration position sensor, and using said determined position coordinates to register said images of said chamber in said frame of reference.

81. A method of mapping a chamber of a heart according to claim 71 wherein said condition is an electrical condition.

82. A method of mapping a chamber of a heart according to claim 71 wherein said condition is a mechanical condition.

83. A method of mapping a chamber of a heart according to claim 71 wherein said condition is an electromechanical condition.

84. A method of mapping a chamber of a heart according to claim 71 wherein said chamber is a left ventricle.

85. A method of mapping a chamber of a heart according to claim 71 wherein said at least one sensor comprises a position sensor capable of providing said three-dimensional position information, said position further providing mechanical condition information.

86. A method of mapping a chamber of a heart according to claim 71 wherein said at least one sensor comprises a position sensor capable of providing said three-dimensional position information and an electrode for sensing electrical information.

87. A method of mapping a chamber of a heart according to claim 71 wherein said at least one sensor comprises an electromagnetic sensor, said electromagnetic sensor generating signals responsive to the strength of a magnetic field external to the patient, said signals indicative of the three-dimensional position of the sensor in said frame of reference.

88. A method of mapping a chamber of a heart according to claim 71 which further comprises the step of creating a map of said chamber from said acquired condition and position information.

* * * * *